(12) United States Patent
Pflueger et al.

(10) Patent No.: US 8,146,600 B2
(45) Date of Patent: Apr. 3, 2012

(54) APPARATUS AND METHODS FOR TREATING SLEEP APNEA

(75) Inventors: D. Russell Pflueger, Monarch Beach, CA (US); Christopher Paul Thompson, Austin, TX (US)

(73) Assignee: Quiescence Medical, Inc., Irvine, CA (US)

( * ) Notice: Subject to any disclaimer, the term of this patent is extended or adjusted under 35 U.S.C. 154(b) by 325 days.

(21) Appl. No.: 11/774,528

(22) Filed: Jul. 6, 2007

(65) Prior Publication Data

US 2008/0035158 A1    Feb. 14, 2008

Related U.S. Application Data

(63) Continuation-in-part of application No. 10/624,915, filed on Jul. 22, 2003, now Pat. No. 7,992,566, and a continuation-in-part of application No. 10/748,761, filed on Dec. 30, 2003, now Pat. No. 7,381,222, and a continuation-in-part of application No. 10/541,255, filed on Mar. 27, 2006, now Pat. No. 8,104,478.

(60) Provisional application No. 60/819,232, filed on Jul. 6, 2006.

(51) Int. Cl.
| | |
|---|---|
| *A61F 5/37* | (2006.01) |
| *A61F 13/00* | (2006.01) |
| *A61F 5/56* | (2006.01) |
| *A61F 2/06* | (2006.01) |
| *A61B 5/08* | (2006.01) |
| *A61N 1/00* | (2006.01) |

(52) U.S. Cl. ........ 128/848; 128/846; 600/529; 602/902; 607/42; 623/1.2

(58) Field of Classification Search .................. 600/529; 128/848; 607/42; 623/1.2; 602/902
See application file for complete search history.

(56) References Cited

U.S. PATENT DOCUMENTS 2,574,623 A    1/1948   Clyde
(Continued)

FOREIGN PATENT DOCUMENTS

DE    19920114 A1    11/2000
(Continued)

OTHER PUBLICATIONS

PCT International Search Report and Written Opinion for PCT/US07072992, Applicant: Quiescence Medical, Inc., Forms PCT/ISA/210, PCT/ISA/220 and PCT/ISA/237, dated Jan. 14, 2008, 16 pages.

(Continued)

*Primary Examiner* — Patricia Bianco
*Assistant Examiner* — Brandon Jackson
(74) *Attorney, Agent, or Firm* — William A. English; Vista IP Law Group LLP

(57) ABSTRACT

Apparatus and methods are provided for treating sleep apnea, snoring, and the like using an implant within an oropharyngeal region adjacent an anterior longitudinal ligament. The implant includes an endless loop defining a curved central region between first and second regions in a horizontal plane. The central region is vertically narrow relative to the first and second regions, and the first and second regions are compressible vertically to allow the first region to be directed through or behind the ligament adjacent the oropharyngeal region such that the central region is disposed within or behind the ligament. The first region is resiliently expandable after passing through or behind the ligament to contact tissue adjacent the oropharyngeal region. The first and second regions are compressible into a "C" shape within the horizontal plane, yet biased to expand and apply a force to dilate the tissue adjacent the oropharyngeal region.

23 Claims, 18 Drawing Sheets

U.S. PATENT DOCUMENTS

| | | |
|---|---|---|
| 3,132,647 A | 5/1964 | Corniello |
| 3,993,078 A | 11/1976 | Bergentz et al. |
| 3,998,209 A | 12/1976 | Macvaugh |
| 4,198,967 A | 4/1980 | Dror |
| 4,304,227 A | 12/1981 | Samelson |
| 4,572,186 A | 2/1986 | Gould et al. |
| 4,580,568 A | 4/1986 | Gianturco |
| 4,665,918 A | 5/1987 | Garza et al. |
| 4,676,240 A | 6/1987 | Gardy |
| 4,732,152 A | 3/1988 | Wallsten et al. |
| 4,794,924 A | 1/1989 | Eliachar |
| 4,803,075 A | 2/1989 | Wallace et al. |
| 4,821,715 A | 4/1989 | Downing |
| 4,830,008 A | 5/1989 | Meer |
| 4,848,343 A | 7/1989 | Wallsten et al. |
| 4,875,480 A | 10/1989 | Imbert |
| 4,950,227 A | 8/1990 | Savin et al. |
| 4,978,323 A | 12/1990 | Freedman |
| 5,007,926 A | 4/1991 | Derbyshire |
| 5,026,377 A | 6/1991 | Burton et al. |
| 5,037,427 A | 8/1991 | Harada et al. |
| 5,046,512 A | 9/1991 | Murchie |
| 5,048,518 A | 9/1991 | Ellachar et al. |
| 5,052,409 A | 10/1991 | Tepper |
| 5,059,211 A | 10/1991 | Stack et al. |
| 5,061,275 A | 10/1991 | Wallsten et al. |
| 5,064,435 A | 11/1991 | Porter |
| 5,065,756 A | 11/1991 | Rapoport |
| 5,071,407 A | 12/1991 | Termin et al. |
| 5,078,720 A | 1/1992 | Burton et al. |
| 5,117,816 A | 6/1992 | Shapiro |
| 5,133,354 A | 7/1992 | Kallok |
| 5,147,370 A | 9/1992 | McNamara et al. |
| 5,176,618 A | 1/1993 | Freedman |
| 5,178,156 A | 1/1993 | Takishima et al. |
| 5,190,053 A | 3/1993 | Meer |
| 5,201,757 A | 4/1993 | Heyn et al. |
| 5,204,382 A | 4/1993 | Wallace et al. |
| 5,258,028 A | 11/1993 | Ersek et al. |
| 5,281,219 A | 1/1994 | Kallok |
| 5,284,161 A | 2/1994 | Karell |
| 5,290,289 A | 3/1994 | Sanders et al. |
| 5,292,331 A | 3/1994 | Boneau |
| 5,306,294 A | 4/1994 | Winston et al. |
| 5,355,874 A | 10/1994 | Bertram |
| 5,360,401 A | 11/1994 | Turnland |
| 5,372,600 A | 12/1994 | Beyar et al. |
| 5,383,926 A | 1/1995 | Lock et al. |
| 5,441,515 A | 8/1995 | Khosravi et al. |
| 5,451,406 A | 9/1995 | Lawin et al. |
| 5,456,662 A | 10/1995 | Edwards et al. |
| 5,474,563 A | 12/1995 | Myler et al. |
| 5,476,505 A | 12/1995 | Limon |
| 5,494,029 A | 2/1996 | Lane et al. |
| 5,514,131 A | 5/1996 | Edwards et al. |
| 5,534,007 A | 7/1996 | St. Germain et al. |
| 5,540,733 A | 7/1996 | Testerman et al. |
| 5,571,135 A | 11/1996 | Fraser et al. |
| 5,582,184 A | 12/1996 | Erickson et al. |
| 5,591,216 A | 1/1997 | Testerman et al. |
| 5,603,698 A | 2/1997 | Roberts et al. |
| 5,611,355 A | 3/1997 | Hilsen |
| 5,618,299 A | 4/1997 | Khosravi et al. |
| 5,632,771 A | 5/1997 | Boatman et al. |
| 5,642,737 A | 7/1997 | Parks |
| 5,643,309 A | 7/1997 | Myler et al. |
| 5,649,540 A | 7/1997 | Alvarez et al. |
| 5,664,567 A | 9/1997 | Linder |
| 5,669,377 A | 9/1997 | Fenn |
| 5,674,191 A | 10/1997 | Edwards et al. |
| 5,682,903 A | 11/1997 | Meade |
| 5,683,451 A | 11/1997 | Lenker et al. |
| 5,709,703 A | 1/1998 | Lukic et al. |
| 5,718,224 A | 2/1998 | Muchin |
| 5,718,702 A | 2/1998 | Edwards |
| 5,720,275 A | 2/1998 | Patil et al. |
| 5,738,114 A | 4/1998 | Edwards |
| 5,772,668 A | 6/1998 | Summers et al. |
| 5,776,142 A | 7/1998 | Gunderson |
| 5,791,341 A | 8/1998 | Bullard |
| 5,792,067 A | 8/1998 | Karell |
| 5,792,478 A | 8/1998 | Lawin et al. |
| 5,797,952 A | 8/1998 | Klein |
| 5,800,379 A | 9/1998 | Edwards |
| 5,815,904 A | 10/1998 | Clubb et al. |
| 5,836,966 A | 11/1998 | St. Germain |
| 5,843,021 A | 12/1998 | Edwards et al. |
| 5,868,138 A | 2/1999 | Halstrom |
| RE36,120 E | 3/1999 | Karell |
| 5,893,365 A | 4/1999 | Anderson |
| 5,897,579 A | 4/1999 | Sanders |
| 5,911,752 A | 6/1999 | Dustrude et al. |
| 5,922,006 A | 7/1999 | Sugerman |
| 5,950,624 A | 9/1999 | Hart |
| 5,954,050 A | 9/1999 | Christopher |
| 5,970,975 A | 10/1999 | Estes et al. |
| 5,979,456 A | 11/1999 | Magovern |
| 5,980,533 A | 11/1999 | Holman |
| 5,983,136 A | 11/1999 | Kamen |
| 5,988,170 A | 11/1999 | Thomas |
| 6,004,342 A | 12/1999 | Filis |
| 6,019,779 A | 2/2000 | Thorud et al. |
| 6,022,343 A | 2/2000 | Johnson et al. |
| 6,027,516 A | 2/2000 | Kolobow et al. |
| 6,027,863 A | 2/2000 | Donadio, III |
| 6,033,394 A | 3/2000 | Vidlund et al. |
| 6,058,931 A | 5/2000 | Muchin |
| 6,090,115 A | 7/2000 | Beyar et al. |
| 6,092,523 A | 7/2000 | Belfer |
| 6,098,616 A | 8/2000 | Lundy, Jr. et al. |
| 6,106,541 A | 8/2000 | Hurbis |
| 6,110,164 A | 8/2000 | Vidlund |
| 6,123,082 A | 9/2000 | Berthon-Jones |
| 6,126,611 A | 10/2000 | Bourgeois et al. |
| 6,126,657 A | 10/2000 | Edwards |
| 6,129,084 A | 10/2000 | Bergerson |
| 6,132,460 A | 10/2000 | Thompson |
| 6,132,461 A | 10/2000 | Thompson |
| 6,161,541 A | 12/2000 | Woodson |
| 6,161,542 A | 12/2000 | Halstrom |
| 6,171,314 B1 | 1/2001 | Rotramel |
| 6,183,493 B1 | 2/2001 | Zammit |
| 6,238,411 B1 | 5/2001 | Thorner |
| 6,238,430 B1 | 5/2001 | Klumb et al. |
| 6,240,316 B1 | 5/2001 | Richmond et al. |
| 6,248,122 B1 | 6/2001 | Klumb et al. |
| 6,250,307 B1 | 6/2001 | Conrad et al. |
| 6,254,631 B1 | 7/2001 | Thompson |
| 6,257,236 B1 | 7/2001 | Dutkiewicz |
| 6,270,512 B1 | 8/2001 | Rittmann |
| 6,273,876 B1 | 8/2001 | Klima et al. |
| 6,305,376 B1 | 10/2001 | Thorton |
| 6,306,141 B1 | 10/2001 | Jervis |
| 6,312,463 B1 | 11/2001 | Rourke et al. |
| 6,325,064 B1 | 12/2001 | Thorton |
| 6,328,753 B1 | 12/2001 | Zammit |
| 6,329,352 B1 | 12/2001 | Meyer et al. |
| 6,345,202 B2 | 2/2002 | Richmond et al. |
| 6,358,274 B1 | 3/2002 | Thompson |
| 6,363,935 B1 | 4/2002 | Boussignac |
| 6,371,112 B1 | 4/2002 | Bibi |
| 6,371,953 B1 | 4/2002 | Beyar et al. |
| 6,371,979 B1 | 4/2002 | Beyar et al. |
| 6,374,824 B1 | 4/2002 | Thorton |
| 6,379,311 B1 | 4/2002 | Gaumond et al. |
| 6,386,199 B1 | 5/2002 | Alfery |
| 6,390,096 B1 | 5/2002 | Conrad et al. |
| D458,679 S | 6/2002 | Thompson |
| 6,401,717 B1 | 6/2002 | Conrad et al. |
| 6,406,490 B1 | 6/2002 | Roth |
| 6,408,852 B2 | 6/2002 | Tielemans |
| 6,415,796 B1 | 7/2002 | Conrad et al. |
| 6,419,641 B1 | 7/2002 | Mark et al. |
| 6,427,686 B2 | 8/2002 | Augustine et al. |
| 6,431,174 B1 | 8/2002 | Knudson et al. |
| 6,432,128 B1 | 8/2002 | Wallace et al. |
| 6,439,238 B1 | 8/2002 | Brenzel et al. |

| | | |
|---|---|---|
| 6,447,522 B2 | 9/2002 | Gambale et al. |
| 6,450,169 B1 | 9/2002 | Conrad et al. |
| 6,453,905 B1 | 9/2002 | Conrad et al. |
| 6,474,339 B1 | 11/2002 | Grosbois et al. |
| 6,475,232 B1 | 11/2002 | Babbs et al. |
| 6,485,524 B2 | 11/2002 | Strecker |
| 6,488,700 B2 | 12/2002 | Klumb et al. |
| 6,502,574 B2 | 1/2003 | Stevens et al. |
| 6,513,530 B2 | 2/2003 | Knudson et al. |
| 6,513,531 B2 | 2/2003 | Knudson et al. |
| 6,516,806 B2 | 2/2003 | Knudson et al. |
| 6,523,541 B2 | 2/2003 | Knudson et al. |
| 6,523,542 B2 | 2/2003 | Knudson et al. |
| 6,523,543 B2 | 2/2003 | Conrad et al. |
| 6,546,936 B2 | 4/2003 | Knudson et al. |
| 6,578,580 B2 | 6/2003 | Conrad et al. |
| 6,601,584 B2 | 8/2003 | Knudson et al. |
| 6,601,585 B1 | 8/2003 | Conrad et al. |
| 6,626,181 B2 | 9/2003 | Knudson et al. |
| 6,634,362 B2 | 10/2003 | Conrad et al. |
| 6,636,767 B1 | 10/2003 | Knudson et al. |
| 6,742,524 B2 | 6/2004 | Knudson et al. |
| 6,793,672 B2 | 9/2004 | Khosravi et al. |
| 6,955,172 B2 | 10/2005 | Nelson et al. |
| 7,188,627 B2 | 3/2007 | Nelson et al. |
| 7,363,926 B2 | 4/2008 | Pflueger |
| 7,381,222 B2 | 6/2008 | Pflueger |
| 2001/0025642 A1 | 10/2001 | Conrad et al. |
| 2001/0044587 A1 | 11/2001 | Conrad et al. |
| 2001/0052344 A1 | 12/2001 | Doshi |
| 2002/0035994 A1 | 3/2002 | Stevens et al. |
| 2002/0040712 A1 | 4/2002 | Chou |
| 2002/0056462 A1 | 5/2002 | Conrad et al. |
| 2002/0108618 A1 | 8/2002 | Conrad et al. |
| 2002/0189727 A1 | 12/2002 | Peterson |
| 2003/0149445 A1 | 8/2003 | Knudson et al. |
| 2003/0149488 A1 | 8/2003 | Metzger et al. |
| 2004/0010308 A1 | 1/2004 | Zafrir-Pachter et al. |
| 2004/0020492 A1 | 2/2004 | Durbrul et al. |
| 2004/0045555 A1 | 3/2004 | Nelson et al. |
| 2004/0045556 A1 | 3/2004 | Nelson et al. |
| 2004/0049102 A1 | 3/2004 | Nelson et al. |
| 2004/0139975 A1 | 7/2004 | Nelson et al. |
| 2004/0172054 A1 | 9/2004 | Metzger et al. |
| 2004/0199045 A1 | 10/2004 | Knudson et al. |
| 2006/0235264 A1 * | 10/2006 | Vassallo .................. 600/37 |
| 2007/0193587 A1 | 8/2007 | Boucher et al. |

FOREIGN PATENT DOCUMENTS

| | | |
|---|---|---|
| EP | 0292936 A2 | 11/1988 |
| EP | 0706808 A1 | 4/1996 |
| SU | 1553140 A1 | 3/1990 |
| WO | 0059398 | 10/2000 |
| WO | 0119301 | 3/2001 |
| WO | 0123039 | 4/2001 |

OTHER PUBLICATIONS

Office Actions and Applicant Responses for related U.S. Appl. No. 10/624,915, dated Jan. 24, 2005 to Apr. 27, 2009, 188 pages.

EPO Office Action for related EP Patent Application No. 03800323. 2-2310, May 14, 2007 to Nov. 19, 2007, 19 pages.

Office Actions and Applicant Responses for related U.S. Appl. No. 11/126,649, Jun. 30, 2006 to Jul. 19, 2007, 59 pages.

Office Actions and Applicant Responses for related U.S. Appl. No. 10/748,761, Nov. 13, 2006 to Aug. 30, 2007, 47 pages.

Office Actions and Applicant Responses for related U.S. Appl. No. 12/052,540, dated Oct. 23, 2008 to Jun. 15, 2009, 28 pages.

Office Actions and Applicant Responses for related U.S. Appl. No. 10/541,255, dated Feb. 3, 2009 to Jul. 9, 2009, 32 pages.

* cited by examiner

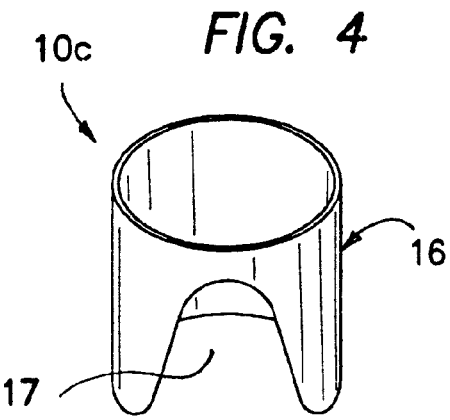
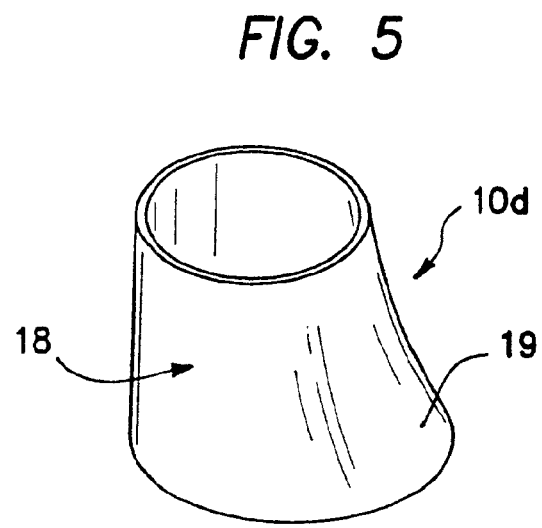
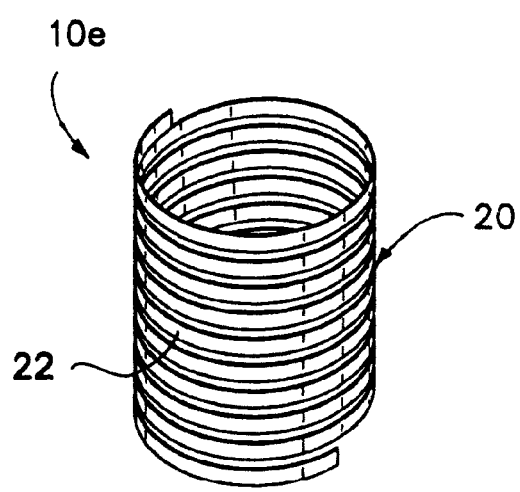
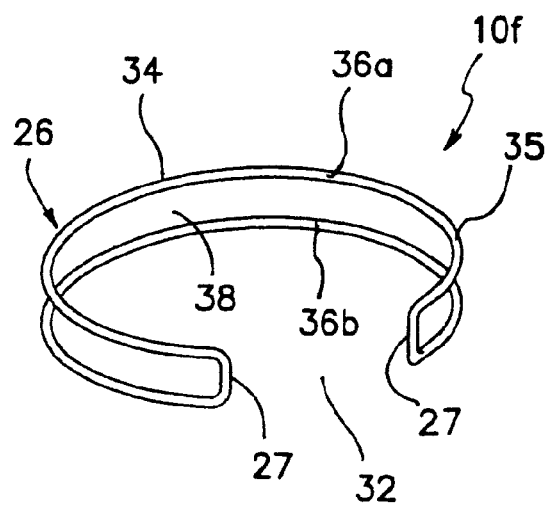

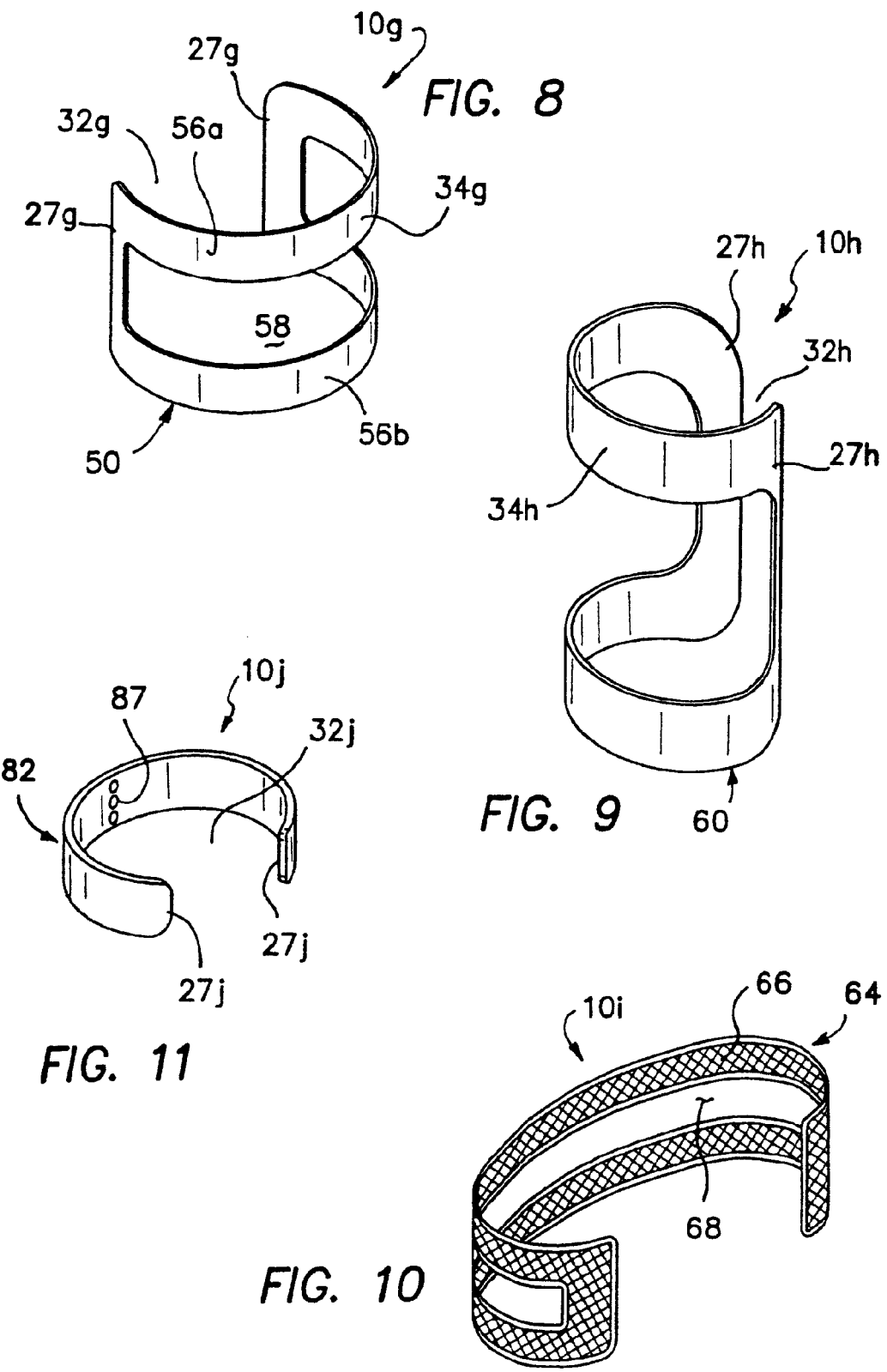

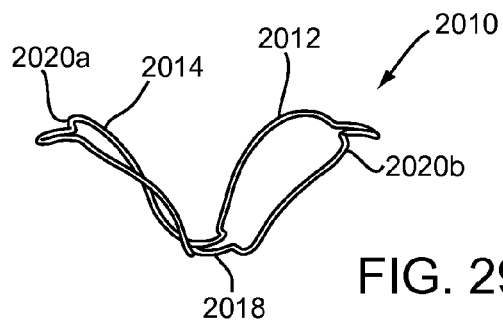
FIG. 29A
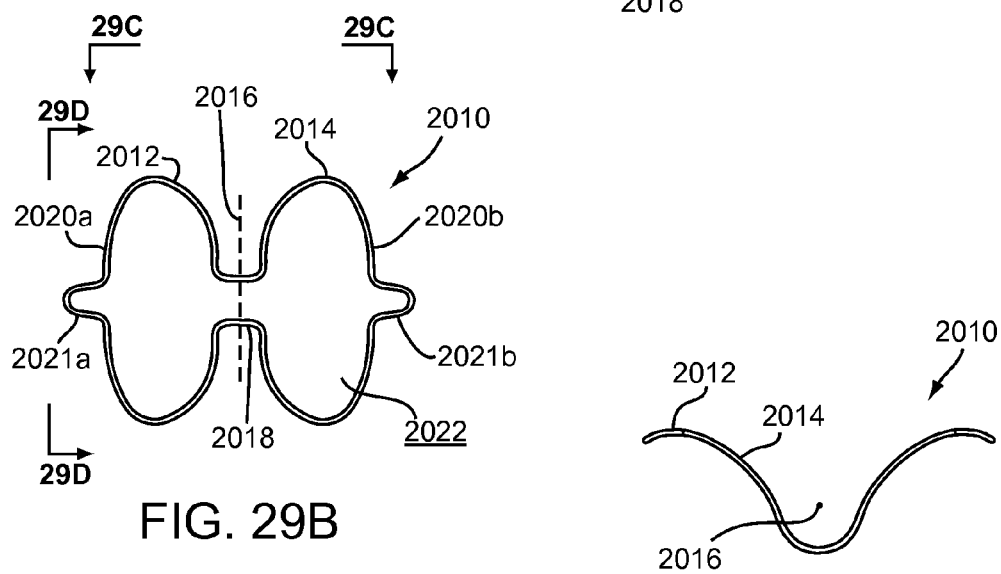
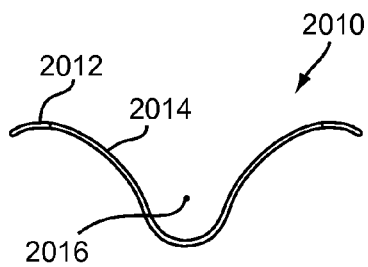
FIG. 29B
FIG. 29C
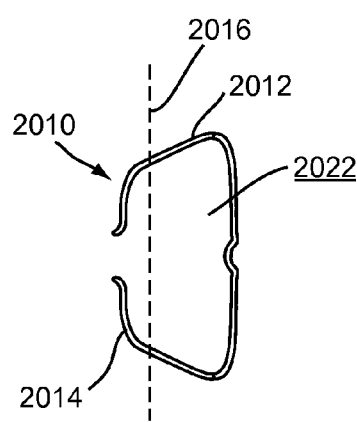
FIG. 29D

APPARATUS AND METHODS FOR TREATING SLEEP APNEA

This application claims benefit of provisional application Ser. No. 60/819,232, filed Jul. 6, 2006, and is a continuation-in-part of application Ser. Nos 10/624,915, filed Jul. 22, 2003, now U.S. Pat. No. 7,992,566, Ser. No. 10/478,761, filed Dec. 30, 2003, now U.S. Pat. No. 7,381,222, and Ser. No. 10/541,255, filed Mar. 27, 2006, now U.S. Pat. No. 8,104,478 the entire disclosures of which are expressly incorporated by reference herein.

BACKGROUND

The present invention generally relates to apparatus and methods for treating sleep apnea, snoring, and/or other breathing disorders, and more specifically relates to apparatus for placement in the oropharyngeal region of a human or animal and to methods for treating sleep apnea, snoring, and/or other breathing disorders.

Sleep apnea is a sleep-related breathing disorder that is thought to affect between one and ten percent (1-10%) of the adult population. Recent epidemiologic data indicate that two percent (2%) of women and four percent (4%) of men between the ages of thirty (30) and sixty (60) years meet the minimum diagnostic criteria for sleep apnea syndrome, representing more than ten million individuals in the United States. It is a disorder with significant morbidity and mortality, contributing to increased risk of hypertension, cardiac arrhythmias, stroke, and cardiovascular death. Another common sleep-related breathing disorder is snoring, which may be associated with or independent of sleep apnea.

The apparatus and methods described herein may aid in treating snoring and/or various degrees of hypopnea and apnea that occur due to pathological disturbances in the sleep process. One of the main reasons for sleep disturbance is relaxation of the tongue and pharyngeal walls to varying degrees during the several stages of sleep. When fully awake, these tissues have normal tone as air passes in and out of the lungs during respiration. However, during sleep, the musculature supporting these tissues relaxes. As air is inspired, the tongue and walls of the pharynx collapse, causing snoring or more seriously, causing partial or complete obstruction of the airway.

Obstructive sleep apnea occurs due to a collapse of soft tissue within the upper airway during sleep. The ongoing force of inspiration serves to generate increasingly negative pressure within the pharynx, causing further collapse. The lack of respiration results in inadequate blood oxygenation, and rising carbon dioxide levels. The cardiovascular response produces an increase in the blood pressure and pulse. Cardiac arrhythmias often occur. The carbon dioxide increase and oxygen desaturation triggers a transition to a lighter sleep stage, usually without wakefulness. This transition brings a return to tonicity of the muscles of the upper airway, allowing normal breathing to resume. The person then returns to deeper stages of sleep and the process is repeated. The disease is quantified in terms of respiratory disturbances per hour. Mild disease begins at ten per hour, and it is not uncommon to find patients with indices of about one hundred or more.

Not surprisingly, sleep is extremely fragmented and of poor quality in persons suffering from sleep apnea. As a result, such persons typically feel tired upon wakening and may fall asleep at inappropriate times during the day. All aspects of quality of life, from physical and emotional health, to social functioning are impaired by obstructive sleep apnea.

Continuous Positive Airway Pressure ("CPAP"), disclosed for example in U.S. Pat. No. 5,065,756, is a popular non-surgical treatment for patients suffering from sleep apnea. CPAP is administered by means of a mechanical unit that delivers pressurized room air to the nasal passage, or airway, through a nose mask that is worn by the patient during sleep. Pressurized air enters from the CPAP unit through the nose when a person is sleeping, and opens the airway from the inside almost as if the air were an internal splint. The correct pressure for the individual is determined in a sleep laboratory. If the nasal airway admits the flow of air, CPAP has in many cases offered immediate relief Unfortunately however, compliance with, and long-term acceptance of this treatment are generally poor. Studies have shown that between twenty and fifty percent (20%-50%) of patients fail to use nasal CPAP as prescribed. Problems associated with CPAP include excessive dryness of the mouth and throat, mucous congestion, sinusitis, and rhinorrhea. Breathing against positive air pressure is also discomforting to many patients.

Other non-surgical treatments for sleep apnea include the use of tongue retaining devices and other oral appliances that hold and/or pull the tongue or jaw in a forward position to open the airway by reducing collapse of the soft palate and/or tongue. These devices also suffer from poor compliance rates, and are usually associated with degenerative changes in the temporomandibular joint.

Surgical procedures have also been proposed and/or practiced for the treatment of moderate to severe sleep apnea. Uvulopalatopharyngoplasty ("UPPP") is a surgical procedure used to treat obstructive sleep apnea. In UPPP, any remaining tonsillar tissue and a portion of the soft palate is removed. The procedure increases the width of the airway at the throat opening. However, UPPP does not address apnea caused by obstructions deeper in the throat and airway, for example, apnea resulting from collapse of tissue near the base of tongue or in the oropharyngeal region of the airway.

LAUP, or Laser-Assisted Uvulopalatoplasty, is a modification of the above-mentioned technique, but has not proven particularly useful for sleep apnea. These surgical techniques are extremely invasive, requiring general anesthesia, and a prolonged, painful recovery.

Radio frequency tissue ablation (RFTA) with the trade name "Somnoplasty", has been used to shrink the soft palate, uvula and reduce tongue volume in the treatment of snoring and obstructive sleep apnea. Somnoplasty utilizes a radiofrequency tool that generates heat to create coagulative lesions at specific locations within the upper airway. The lesions created by the procedure are naturally resorbed in approximately three to eight weeks, reducing excess tissue volume and increasing the airway opening. Like UPPP and LAUP, more than one session is typically required and it does not address sleep apnea resulting from tissues deeper in the throat than the upper airway.

Another area of surgical interest lies in techniques designed to pull the tongue anteriorly. The most recent such surgical system designed to treat snoring (as well as obstructive sleep apnea) was approved by the FDA in February 1998. Known as the tongue suspension procedure (with the trade name Repose), it is intended to pull the tongue forward, thereby keeping the tongue from falling into the airway during sleep. The system utilizes a bone screw inserted into the mandible. The screw attaches to a non-absorbable suture which travels the length of the tongue and back. Similarly, the hyoid bone can be drawn anteriorly with two distinct screws, also attached to the mandible.

Techniques have also been developed for treating, specifically, the condition of snoring. For example, U.S. Pat. No.

6,250,307 to Conrad et al. discloses a method for treating snoring of a patient that includes embedding a fibrosis-inducing implant into a soft palate of a patient in order to alter a dynamic response of a soft palate to airflow. The disclosed methods are specifically designed to reduce the audibility of snoring but do not adequately address the more serious condition of sleep apnea.

Concepts relating to implants in the pharyngeal area have been described in German publication DE 19,920,114 to Fege, published Nov. 9, 2000, which discloses transverse implant bands attached at one end to the cervical vertebra via surgical slits through the tongue, tonsils, and pharyngeal tissue.

Other pharyngeal implants have been described in U.S. Publication No. 2003/0149488 to Metzger et al., now U.S. Pat. No. 7,017,582, which discloses one or more fibrosis-inducing braided implants placed in the pharyngeal wall to stiffen the tissue, i.e., by encouraging tissue ingrowth and inducing a fibrotic response. Multiple disconnected separate devices are shown implanted in either transverse or longitudinal orientations. The preferred devices are about two millimeters (2 mm) in diameter and ten to twenty millimeters (10 to 20 mm) in length. A sheet of fibrosis-inducing material is also disclosed. Dimensional attributes used to calculate the design included a thirty millimeter (30 mm) thick pharyngeal wall, a 4.7 mm anterior-posterior airway diameter, and a 6.7 mm lateral airway diameter. Such an approach, however, ignores the need for mechanical stability and sufficient strength and resiliency to effectively resist simultaneous collapse of large portions of the posterior and lateral pharyngeal wall.

These conventional devices and treatments continue to suffer poor cure rates. The failures may lie in their inability to maintain patency in the retropalatal region and retroglossal region (the caudal margin of the soft palate to the base of the epiglottis). The poor success rates combined with high morbidity, contribute to an ongoing need for more effective treatments for sleep apnea and/or snoring.

SUMMARY

The present invention is directed to apparatus and methods to treat, for example, to substantially eliminate or at least reduce the occurrence of, sleep apnea, snoring, and/or other sleep-related breathing disorders. The apparatus and methods may be relatively straightforward in structure and use, may be minimally invasive, and/or may provide substantial benefits over conventional techniques in controlling sleep apnea and/or snoring.

In accordance with one embodiment, an implant is provided that includes a substantially continuous loop structure including a curved central region between first and second regions in a horizontal plane. The first and second regions may be compressible towards one another such that the implant defines a generally "C" shape about a vertical axis extending from the horizontal plane, the first and second regions being biased to open away from the vertical axis within the horizontal plane when unconstrained such that the first and second regions apply a force to dilate tissue adjacent the oropharyngeal region when the implant is disposed within the oropharyngeal region. The central region of the implant may be vertically narrow relative to the first and second regions, at least one of the first and second regions being compressible vertically to allow the at least one of the first and second regions to be directed through or behind the ligament adjacent the oropharyngeal region such that the central region is disposed within or behind the ligament, the at least one of the first and second regions being resiliently expandable after passing through or behind the ligament.

In accordance with another embodiment, an apparatus is provided for implantation within an oropharyngeal region adjacent a ligament that includes an implant including a curved central region between first and second regions in a horizontal plane, the central region being vertically narrow relative to the first and second regions. At least one of the first and second regions is compressible vertically to allow the at least one of the first and second regions to be directed through or behind the ligament adjacent the oropharyngeal region such that the central region is disposed within or behind the ligament, the at least one of the first and second regions being resiliently expandable after passing through or behind the ligament. The first and second regions may also be compressible towards one another within the horizontal plane such that the implant defines a generally "C" shape about a vertical axis extending from the horizontal plane, the first and second regions being biased to open away from the vertical axis within the horizontal plane when unconstrained such that the first and second regions apply a force to dilate tissue adjacent the oropharyngeal region when the implant is disposed within the oropharyngeal region.

In accordance with still another embodiment, a system is provided for treating sleep apnea, snoring, and/or other breathing disorders that includes an implant including a curved central region between first and second regions in a horizontal plane, and a needle coupled to the first end region by a filament for insertion through a ligament adjacent an oropharyngeal region. The central region is vertically narrow relative to the first and second regions, and at least the first region is compressible vertically to allow the first region to be directed through or behind the ligament adjacent the oropharyngeal region when the needle and filament are inserted through or behind the ligament such that the central region is disposed within or behind the ligament, the first region being resiliently expandable after passing through or behind the ligament. The first and second regions may also foldable or otherwise compressible towards one another within the horizontal plane such that the implant defines a generally "C" shape about a vertical axis extending from the horizontal plane. The first and second regions may be biased to open away from the vertical axis within the horizontal plane when unconstrained such that the first and second regions apply a force to dilate tissue adjacent the oropharyngeal region when the implant is disposed within the oropharyngeal region. The first and second regions may increase a surface area contacting adjacent tissue, which may facilitate dilating, opening, or otherwise treating tissue adjacent the oropharyngeal region.

In accordance with yet another embodiment, an apparatus is provided that includes an appliance sized and structured to be substantially permanently or temporarily implanted or placed in an oropharyngeal region of a human or animal. For example, the apparatus may be implanted for long term usage and/or for relatively long durations, such as at least about one (1) week or about one (1) month, for example, at least about six (6) months, at least about one (1) year, about five (5) years or longer), The apparatus may include any material or materials suitable for placement in the pharyngeal region that may be effective to reinforce tissues of the region in order to provide support to these tissues against collapse such that a patient can breathe more effectively than the patient would breathe without the material or materials placed in the region.

In one embodiment, the apparatus generally includes an appliance sized and structured to be placed in a given position in the oropharyngeal region, other than to facilitate a surgical procedure, and to be effective, when placed in the given position, to treat sleep apnea and/or snoring in a human and or animal (hereinafter, sometimes "patient"). In addition, the appliance is structured to be effective, when so placed, to provide at least one additional benefit relative to a different device that is sized and structured for placement in a position in the patient other than in the given position in the oropharyngeal region. In one embodiment, the appliance is structured to provide an enhanced compliance with normal, healthy functioning of the oropharyngeal region of a patient relative to such a different device, for example, a stent that is not specifically structured to be utilized for treatment of sleep apnea. For example, the apparatus is structured to have an enhanced ability, relative to such a different device, to be tolerated, e.g., comfortably tolerated, by the human or animal while the apparatus is in the given position in the oropharyngeal region, such as when the human or animal is awake or is naturally sleeping.

The appliance may be structured to have an enhanced ability, relative to such a different device, to provide support against collapse of the oropharyngeal region during natural sleep, as well as to allow proper closure of an airway in the oropharyngeal region during swallowing.

In one embodiment, the appliance is sized and structured so that, when so placed in the given position in the oropharyngeal region, the appliance is located substantially entirely within the pharyngeal region including, for example, the oropharyngeal region. The apparatus is sized and structured to be temporarily placed in the given position or to be placed in the given position on a relatively long term basis for example, as described elsewhere herein. In addition, the appliance may be structured to resist migration within the oropharyngeal region or outside the oropharyngeal region.

In one embodiment, the appliance includes a curved member, when located outside the body in a resting or at rest position, including spaced apart end portions and a body portion joining the end portions. In this embodiment, the apparatus may be designed such that when the apparatus is appropriately positioned in the given position with end portions bearing against and supporting adjacent tissue, e.g., the lateral walls of the oropharyngeal region, against collapse. The appliance may be sized and structured such that when the apparatus is appropriately placed in the given position, the end portions are spaced apart anteriorly of the posterior wall of the oropharyngeal region, for example, by a portion of the anterior wall of the oropharyngeal region. In an exemplary embodiment, the appliance expands to form an effective diameter of about thirty two millimeters (32 mm) or greater in order to adequately expand to fill the oropharyngeal region.

If desired, the apparatus may be structured to facilitate removal thereof from the oropharyngeal region. For example, the apparatus may be structured such that when the apparatus is in other than the deployed configuration, for example, when the apparatus is located outside an oropharyngeal region of a human or animal or outside the body of the human or animal in a resting position, the appliance includes a member that has a flexibility and resiliency that allows the appliance to be folded, rolled, or otherwise compressed to take on a relatively smaller radius for facilitating insertion thereof into the oropharyngeal region, for example, through the mouth or oral cavity of the patient. When released into the pharyngeal region, the appliance unfolds, unrolls, or otherwise expands, and provides pressure against one or more portions of the pharyngeal region, providing support thereto and maintaining or achieving patency of the pharyngeal region, for example, whether the patient is awake or is naturally sleeping. In the event that the appliance needs to be removed, the appliance can be designed to reside within the oropharyngeal region with minimal tissue response, for example, with little or substantially no fibrotic tissue response, allowing subsequent removal using standard otolaryngology techniques.

Optionally, the appliance may also have mesh fabric or polymer, e.g., attached to the lateral end portions and/or covering some or all of the central areas of the appliance to improve support and facilitate stability.

The appliance may be sized and structured to allow substantially natural functioning of the oropharyngeal region and the epiglottis when the appliance is located in the given position in the pharyngeal region of the patient.

It will become apparent that various configurations of the apparatus are possible to achieve one or more of the benefits described herein in controlling or otherwise treating sleep apnea, snoring, and/or other breathing disorders. Such configurations may include an appliance having a substantially elliptical configuration, a substantially circular configuration, a substantially rectangular configuration, a substantially cylindrical configuration, a substantially linear configuration, a substantially cross-shaped configuration, a substantially C-shaped configuration, a substantially cuff shaped configuration, a substantially coil shaped configuration, a substantially double concave loop configuration, a substantially bow tie shaped configuration and the like configurations and combinations thereof For example, in an exemplary embodiment, the appliance includes, in a rest position outside the body of a human or animal a curved, flexible, elliptical member having rounded end portions, a length defined between the end portions, and a body portion including a plurality of spaced apart struts extending along at least a substantial portion of the length between the end portions.

In various embodiments, the appliance, when located in the oropharyngeal region, may have a resiliency and flexibility, for example, resiliency and/or flexibility in at least one direction or at least two different directions or at least three different directions, that enables the appliance to provide an appropriate amount of support and reinforcement to oropharyngeal tissues during natural sleep, while enabling substantially normal functioning of the oropharyngeal region and the epiglottis, for example, during swallowing.

The appliance may be formed from elastic material, such as a super-elastic material. A number of suitable elastic and super-elastic materials are well known and can be employed. One particularly useful material is a nickel titanium alloy, known as Nitinol. The appliance may have a hoop strength effective to support the oropharyngeal region against collapse during natural sleep. For example, in one embodiment, the appliance may have a hoop strength in a range of at least about one centimeter (1 cm) water to about four hundred centimeters (400 cm) water or greater.

The apparatus may include an appliance sized and structured to be placed in a position in the oropharyngeal region in proximity to the epiglottis, other than to facilitate a surgical procedure, effective in treating sleep apnea, snoring, and/or other breathing disorders. The appliance may be sized and structured to substantially entirely fit within the oropharyngeal region when placed in position. A portion of the device may also be considered to extend above the oropharyngeal region, e.g., along the lateral portions of the pharynx.

In accordance with another embodiment, the apparatus may include an element placed within the oropharyngeal region that is effective, when so placed to reinforce tissues within the oropharyngeal region in order to support these tissues against collapse and allow substantially normal breathing during sleep.

For example, the element may include at least one strip of material that is structured to be placed within the walls of the oropharyngeal region. For example, the element may include multiple strips of material that are structured and suitable to be implanted within the oropharyngeal tissues, for example, beneath the mucosal tissue, for example, in a spaced apart, substantially horizontal fashion.

In accordance with another embodiment, a method is provided for treating sleep apnea or snoring within an oropharyngeal region adjacent an anterior longitudinal ligament that includes introducing an implant into the oropharyngeal region, the implant comprising a curved central region between first and second regions, the central region being vertically narrow relative to the first and second regions; and introducing the first region through an opening through or behind the ligament, the first region compressing vertically from a relaxed configuration as the first region passes through the opening, until the first region passes through the opening, whereupon the first region resiliently expands towards the relaxed configuration, the central region remaining within the opening.

In accordance with still another embodiment, a method is provided for controlling sleep apnea or snoring in a human or animal having an oropharyngeal region and an anterior longitudinal ligament. A flexible, resilient appliance may be provided sized and structured to be positioned in an oropharyngeal region of a patient, the appliance comprising substantially opposing elongated elements together forming a loop having a generally narrow central region and first and second end regions that are relatively wider than the central region. The appliance may be introduced into the oropharyngeal region by passing the appliance into a lateral or posterior wall of the oropharyngeal region and through or adjacent the anterior longitudinal ligament of the patient such that, upon the appliance being so positioned in the oropharyngeal region, the generally narrow central region is at least partially beneath the posterior wall of the oropharyngeal region and the first and second end portions are located against or within the posterior and right and left lateral walls of the oropharyngeal region.

In accordance with yet another embodiment, a method is provided for treating sleep apnea, snoring, and/or other breathing disorders that includes securing one or more elements to the oropharyngeal region and allowing the elements to provide an opening force against the oropharyngeal walls, such opening force being sufficient to reinforce the walls against collapse during natural sleep while allowing substantially normal functioning of the oropharyngeal region.

In one embodiment, the method may include placing an appliance at least partially submucosally, within the oropharyngeal region of a patient that is effective, when so placed, to maintain patency of the oropharyngeal region. Optionally, the apparatus may be placed substantially entirely submucosally, e.g., in the oropharyngeal region.

The apparatus may be sized to be placed, at least partially, circumscribing an interior hollow passage defined by the pharyngeal region, for example the oropharyngeal region. In a related aspect, the appliance may be sized to be placed circumscribing, at least once, the interior hollow passage defined by the oropharyngeal region.

In another embodiment, the element may include an element that provides a magnetic opening force against collapsing pharyngeal, for example, oropharyngeal, tissues. For example, the element may include an appliance, such as described and shown elsewhere herein, that is at least partially magnetized. More specifically, the element may include two or more magnetic elements having like poles facing one another, to create a magnetic field that can be utilized to provide a useful opening force to the pharyngeal, for example, oropharyngeal, region.

In accordance with still another embodiment, methods for treating sleep apnea and/or snoring in a human or an animal having an oropharyngeal region are provided. In one aspect, the methods generally include providing an appliance, such as any of those described elsewhere herein, in the oropharyngeal region of the human or animal. The appliance, located in the oropharyngeal region, is effective in treating sleep apnea, snoring, and/or other breathing disorders during natural sleep of the human or animal.

In one embodiment, an appliance is placed in the oropharyngeal region that is effective in maintaining patency of the oropharyngeal region during natural sleep of the human or animal. The appliance may be effective in maintaining patency without causing substantial interference with one or more natural functions of the oropharyngeal region or the epiglottis. For example, the appliance may be structured, when placed in the oropharyngeal region, to be effective to support the tissues of the oropharyngeal region against collapse while allowing the oropharyngeal region to close and/or otherwise function consistent with normal swallowing. The apparatus is designed so that, when the appliance is placed in the oropharyngeal region, it is effective in supporting and holding the lateral walls of the oropharyngeal region in an open position, and/or in supporting and holding the tongue of the patient in a forward position, for example, during natural sleep of the patient.

In accordance with yet another embodiment, a method is provided for maintaining patency of a oropharyngeal region of a human or an animal during natural sleep. The method generally includes providing a member in a substantially flat or precurved configuration, the member having a body portion and end portions spaced apart by the body portions, and implanting the member, at least partially submucosally, within the oropharyngeal region.

The member may be effective to provide a substantially constant force against at least a portion of each of a right and left lateral wall of the oropharyngeal region.

For example, the step of implanting may include implanting the member into the oropharyngeal region such that the member is substantially entirely submucosally implanted therein.

In yet another related embodiment, a method is provided for maintaining patency of a pharyngeal region of a human or animal during natural sleep and for purposes other than surgery that includes causing a tissue reaction of a pharyngeal region of the patient, the tissue reaction being effective in at least one of strengthening and stiffening lateral walls of the pharyngeal region. For example, a tissue reaction may be caused by applying an active agent to the walls of the pharyngeal region or, for example, placing at least one member into the lateral walls.

For example, the appliance may be inserted into the oropharyngeal region, for example through the mouth or oral cavity of the patient, or alternatively, through the nasal cavity of the patient, while the appliance is in a first configuration and, thereafter, the appliance may be allowed to reconfigure to a second configuration within the oropharyngeal region.

In yet another aspect, a method for treating sleep apnea and/or snoring includes causing a tissue reaction in an oropharyngeal region of a patient. Such tissue reaction may be effected to cause sufficient support, stiffening, and/or strengthening of targeted oropharyngeal tissues in order to substantially reduce the occurrence of collapse of those tissues during natural sleep of the patient.

For example, a tissue reaction may be caused by one or more of injecting a suitable agent into the tissues, applying wave energy to the tissues, and/or causing mechanical irritation to the tissues in order to provoke a strengthening response.

Each and every feature described herein, and each and every combination of two or more of such features, is included within the scope of the present invention provided that the features included in such a combination are not mutually inconsistent.

These and other aspects of the present invention are apparent in the following detailed description and claims, particularly when considered in conjunction with the accompanying drawings in which like parts bear like reference numerals.

BRIEF DESCRIPTION OF THE DRAWINGS

FIG. 4 is a perspective view of an additional embodiment of an implant similar to that shown in FIG. 2, and including a recessed portion for accommodating an epiglottis of a patient.

FIG. 5 is a perspective view of yet another embodiment of an implant including an extended portion.

FIG. 6 is a perspective view of a further embodiment of an implant having a coiled configuration.

FIGS. 7, 8, and 9 are perspective views of various other embodiments of implants including substantially cuff-shaped configurations of different proportions to accommodate different patient needs.

FIG. 10 is a perspective view of still another embodiment of an implant including a substantially cuff-shaped configuration including a mesh material.

FIG. 11 is a perspective view of a yet further embodiment of an implant including a substantially solid C-shaped configuration having apertures for allowing tissue ingrowth.

FIGS. 29A-29D are perspective, front, top, and side views, respectively, of another embodiment of an implant for treating sleep apnea, snoring, and/or other breathing disorders.

DETAILED DESCRIPTION OF THE EXEMPLARY EMBODIMENTS

Figure 1:
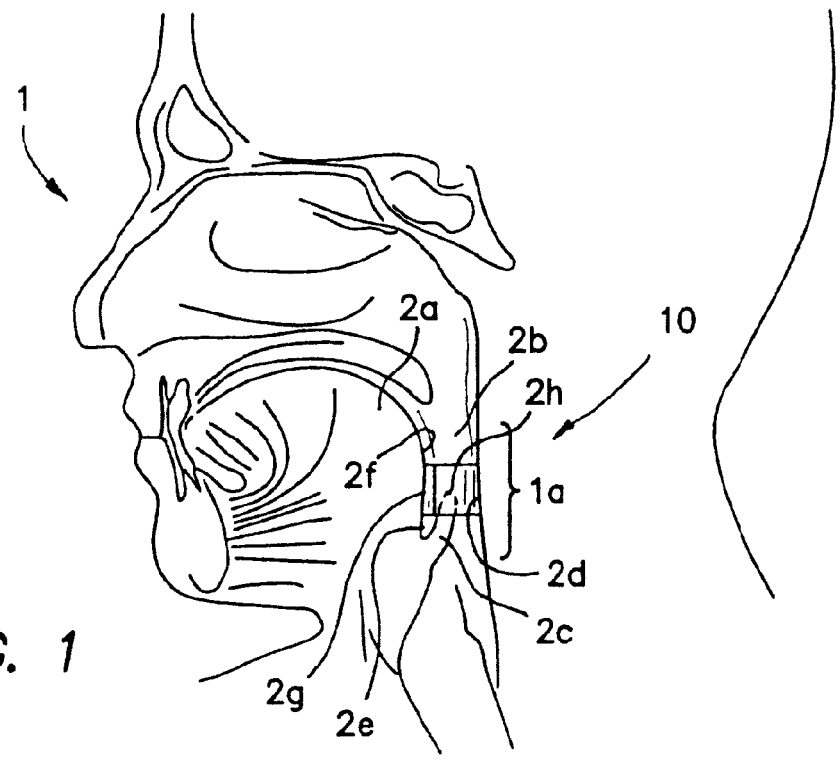
FIG. 1 is a cross-sectional view of a patient's head, showing an exemplary embodiment of an implant positioned in an oropharyngeal region of the patient.

In a broad aspect, the apparatus described herein generally include an implant, stent, or other appliance sized and/or structured to be placed in a given position in an oropharyngeal region of a human or animal patient, other than to facilitate a surgical procedure on the patient, and being effective in treating sleep apnea, snoring, and/or other breathing or sleeping disorders of the patient. The appliance is further effective, when so placed in the given position, to provide at least one additional benefit or advantage relative to a device sized and structured for placement in a different position in a human or animal wherein a "different position" is defined as a position other than the given position.

Additional general information related to the apparatus and methods described herein may be found in co-pending application Ser. Nos. 10/624,915, filed Jul. 22, 2003, 10/478,761, filed Dec. 30, 2003, and 10/541,255, filed Mar. 27, 2006. The entire disclosures of these references and any other references cited therein are expressly incorporated by reference herein. It has been discovered that a number of the devices disclosed in the references identified in these applications, which are conventionally utilized or suggested for utilization in body regions other than the oropharyngeal region and/or to treat conditions other than sleep apnea and/or snoring, can be utilized or modified to be utilized in the oropharyngeal region of a human or an animal in order to treat sleep apnea and/or snoring, in accordance with the present invention. Any such modification or modifications to such conventional devices are considered to be included within the scope of the apparatus of the present invention. In addition, it may be possible to use any of these devices, and any modified such devices, in the oropharyngeal region of a human or an animal in order to treat sleep apnea, snoring, and/or other breathing disorders in the methods described herein. It can be noted that currently there are no stents marketed which are designed to expand to diameters in excess of thirty two millimeters (32 mm).

For example, at least one or more of the following benefits or advantages may be achieved using the apparatus described herein, relative to devices conventionally utilized or suggested for utilization in body regions other then the oropharyngeal region and/or to treat conditions other than sleep apnea and/or snoring, may include at least one or more of the following: the apparatus is structured to be located in the oropharyngeal region and to have an enhanced ability to be tolerated by the human or animal, for example, while the human or animal is awake or is naturally sleeping; the apparatus is structured to provide enhanced resistance to static collapsing forces of the oropharyngeal region and/or hypopharynx; the apparatus is structured to have an enhanced ability to allow for dynamic collapse; the apparatus is structured to have enhanced non-mobility, for example, upon coughing, throat clearing and/or sneezing; the apparatus is structured to have enhanced conformity to the healthy, normal shape of the pharynx; the apparatus is structured to have an enhanced ability to be removable; the apparatus is structured to have an enhanced ability to be deployable under direct vision via nasopharyngoscopy/laryngoscopy; and the like.

In addition, the apparatus described herein may be structured not to substantially interfere with swallowing, respiration, vocalization, mucociliary function, epiglottis functioning, and the like. The apparatus described herein may also be structured to maintain the openness of the oropharyngeal region during natural sleep.

Turning now to the drawings, FIG. 1 shows a cross-sectional anatomical view of a human patient 1. The patient 1 has an exemplary apparatus 10, which may be any of the embodiments described herein, located within the patient's oropharyngeal region 1a in order to substantially control, reduce, eliminate, or otherwise treat sleep apnea, snoring, and/or other breathing disorders.

Snoring and sleep apnea are often caused by a combination of narrowness and low muscle tone of the upper airways. The tongue 2a may fall back and obstruct the airway, possibly leading to an arousal reaction and disturbing the normal sleeping pattern. Other portions of the oropharyngeal region may also collapse. For example, the lateral walls 2b of the oropharyngeal region often become excessively lax and block a free flow of air during respiration. When the patient 1 is supine, for example, when the patient 1 is asleep and lying on his/her back, the relaxed tongue 2a may move inferiorly (down) and posteriorly (back), and/or the lateral walls 2b of the oropharyngeal region may collapse inwardly resulting in a narrower pharynx relative to when the patient 1 is upright. One cause for the narrowing of the pharynx in the supine position may be that the oropharyngeal region 1a and hypopharyngeal region, which have low consistencies, collapse because of lack of direct hard tissue support.

The apparatus 10 may be secured to the pharyngeal region by various methods. For example, the apparatus 10 may be sutured to the pharyngeal region, for example with dissolvable sutures that will allow the apparatus 10 to be held in place while the apparatus 10 becomes fixed to the region by means of tissue ingrowth. Alternatively, the apparatus 10 may be secured to the region by means of a suitable biocompatible adhesive as are presently known in the art. Alternatively still, the apparatus 10 may be secured to the region by being surgically implanted into the region, for example, directly beneath the region's mucosal layer, (hereinafter, "submucosally"), for example, by being pulled, with a surgical needle for example, at least partially into and beneath the mucosal layer such that the apparatus at least partially circumscribes the region.

The apparatus 10 may be designed to provide direct support to at least some of these tissues when the patient 1 is supine and asleep. For example, the apparatus 10 may be structured so that when placed in the given position in oropharyngeal region 1a, the apparatus 10 will push the tongue forward, and/or push the lateral walls 2b away from one another thereby holding the airway patent or open during the time the human or animal is naturally sleeping.

As shown, the apparatus 10 may be sized and structured to be positioned adjacent the epiglottis 2c of patient 1, e.g., but without coming in contact therewith. For example, in one embodiment, the apparatus 10 is designed to overlay a posterior wall 2d of the oropharyngeal region 1a and provide an opening force outwardly against opposing lateral walls 2b of the oropharyngeal region 1a. In other embodiments, the apparatus 10 is designed to rest within a valecullar space 2e and provide a pushing force against the base 2f of the tongue 2a which makes up a portion of the anterior wall 2g of the oropharyngeal region 1a. The valecullar space 2e, as the term is used herein, is defined as being the space between the anterior wall 2g of the throat and the upper tip 2h of the epiglottis 2c down to the conjunction of the epiglottis 2c with the anterior wall 2g of the pharynx.

In any event, the apparatus 10 is designed in such a manner as to substantially prevent the apparatus 10 from interfering substantially with the normal functioning of the tissue around the apparatus 10, particularly with the normal functioning of the epiglottis 2c. The apparatus 10 may include structures (described elsewhere herein) for anchoring or securing the apparatus 10 within the oropharyngeal region 1a in order to prevent the apparatus 10 from migrating away from or out of the given position. The apparatus 10 may be structured to closely and flexibly conform to the size and contours of at least a portion of the oropharyngeal region 1a.

In one embodiment, the apparatus 10 may be said to be effective to provide a support substantially equivalent to the support of tissue and/or muscles of an oropharyngeal region in a healthy, toned state.

As a specific example, the apparatus 10 may be sized and shaped to fit a human patient having a measured anterior-posterior linear distance between the pharyngeal walls, when the patient is awake and not supine, and the tongue and/or other tissues are not fully lax.

The apparatus 10 may be structured to maintain a radial force or pressure, for example, a substantially constant radial force or pressure, against the oropharyngeal region, specifically against the lateral walls of the oropharyngeal region, the posterior portion of the oropharyngeal region, and/or the base of the tongue. The pressure of the apparatus maintained against this region is advantageously sufficient to maintain patency of the oropharyngeal region during natural sleep in a supine position (for example, greater than about ten centimeters (10 cm) of water), and may exert pressure less than that exerted by the surfaces of the oropharyngeal region during swallowing (for example, about four hundred centimeters (400 cm) of water). The apparatus may have hoop strength in a range of about five centimeters (5 cm) of water up to about four hundred centimeters (400 cm) of water. It is further noted that the design of apparatus 10 allows for variable hoop strength as measured along different points about the circumference of the appliance of the apparatus.

The apparatus 10 is designed and structured to allow substantially normal functioning of the oropharyngeal and pharyngeal regions, while maintaining the structural integrity of the apparatus over a long period of time. An important consideration in the design of the apparatus 10 includes the requirement that the apparatus 10 substantially maintain its structural integrity and strength despite the highly dynamic, peristaltic motion of the oropharyngeal and hypopharyngeal regions.

For example, it is known that a human being typically swallows an average of two times a minute throughout the day. This equals around two thousand (200) swallows per day. The force of the swallow varies from one and a half to six pounds (1.5-6 lbs.) of pressure, and the force lasts for about 0.1 to about 0.2 second.

Swallowing also includes the involuntary apposition of the soft palate to the posterior pharyngeal wall, which is believed to last almost a second and producing a pressure of about one hundred sixty millimeters of mercury (160 mm Hg) and initiate pharyngeal peristalsis, i.e., the wavelike muscular contractions that move food along the alimentary canal in the pharyngeal region. This moving front of contraction passes through the pharyngeal constrictors in sequence, traversing the pharynx and hypopharynx at about fifteen centimeters per second (15 cm/s) to reach the upper esophageal sphincter in about one second. The hypopharyngeal contraction lasts about 0.3 to about 0.5 seconds and generates an intraluminal pressure of two hundred millimeters of mercury (200 mm Hg). The apparatus 10 may be designed to flex and contract along with this wave-like motion of the various muscles in the oropharyngeal and hypopharyngeal region.

The appropriate amount of force necessary to provide adequate support to maintain patency and consistent air flow in the oropharyngeal region during sleep, while allowing for the dynamic motion of the pharyngeal region and normal function of the oropharyngeal region and/or hypopharyngeal region, may vary between patients. Therefore, the apparatus 10 may be available in a range of radial forces and sizes in order to suit different individuals. For example, each of the embodiments described herein may be made of resilient and elastic biocompatible materials and all edges and surfaces may be smooth and free of sharp portions, burrs, and/or contaminants.

FIGS. 2-6 show various embodiments of the apparatus 10 that are generally cylindrical or tubular in structure. Except as expressly described herein, each of the apparatus 10a-10e, shown in FIGS. 2-6 respectively, is similar to apparatus 10 and is structured, unless otherwise noted herein, to be utilized for the treatment of sleep apnea, snoring, and/or other breathing disorders, as hereinabove noted.

Figure 2:
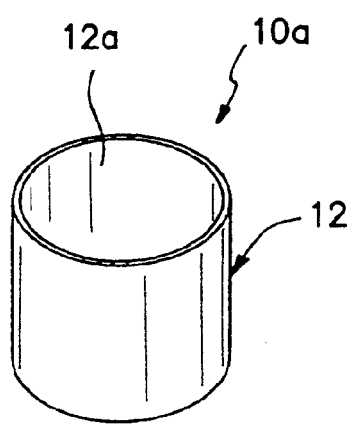
FIG. 2 is a perspective view of an exemplary embodiment of an implant having a substantially solid-walled cylindrical shape.

Turning now specifically to FIG. 2, apparatus 10a is an appliance 12 structured to fit substantially entirely within the oropharyngeal region and at least partially within the valecullar space and/or extending no higher than the upper surface of the base of the tongue in the anterior portion of the apparatus 10a. The posterior portion of the apparatus 10a may be designed to provide additional support above the oropharyngeal region.

The appliance 12 defines a central open or hollow space 12a and may be made of any suitable biocompatible material, for example, stainless steel, Nitinol, Elgiloy, or other metals, plastics (polymeric materials), and the like, and composites and/or combinations thereof.

Figure 3:
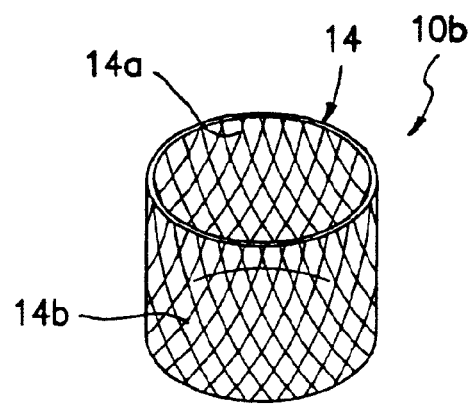
FIG. 3 is a perspective view of another embodiment of an implant having a substantially mesh-walled cylindrical shape.

FIG. 3 shows an apparatus 10b including a substantially cylindrical appliance 14 similar to appliance 12, with the most significant difference being that appliance 14 includes a mesh, braid, weave, or knit, for example a woven fabric, polymer, and/or wire mesh. The mesh appliance 14 defines a central open or hollow space 14a and includes wires 14b made from a super-elastic material, for example, a nickel titanium alloy (to be described in more detail elsewhere herein), such as the alloy known as Nitinol.

FIG. 4 shows an additional apparatus 10c, similar to apparatus 10a, including a solid cylindrical appliance 16 including a feature of a cut-out region 17 defined in the appliance 16, the cut-out region being appropriately sized, shaped, and positioned to accommodate natural movements and functions of the epiglottis of a patient (not shown). Thus, in this embodiment, the apparatus 10c may be fitted to a patient with cut-out portion 17 facing an anterior wall of the oropharyngeal region. The epiglottis is therefore free to move inwardly and outwardly of the appliance by means of the cut-out region.

FIG. 5 shows yet another apparatus 10d, including an appliance 18 having a relatively wider diameter distal or lower portion 19 that may function to anchor or hold the appliance 18 within the valecullar space. When in use, the apparatus 10d is anchored at portion 19 within the vallecular space allowing the epiglottis to function normally within the relatively wider hollow area defined by the lower portion 19.

FIG. 6 shows a further embodiment, specifically an apparatus 10e generally including an appliance 20 having a helical or spiral spring including coils 22 formed, for example, from a super-elastic material, as described elsewhere herein.

FIGS. 7-11 show various other embodiments of implants that are generally non-circumferentially enclosed in structure. Instead, the implants generally define a "C" shape or other open structure, which may define a portion of a circle, ellipse, or other discontinuous periphery. Except as expressly described herein, each of the apparatus 10f-10j, shown in FIGS. 7-11 respectively, may be constructed using materials and/or methods similar to apparatus 10 and/or may be structured, unless otherwise noted herein, to be utilized for the treatment of sleep apnea and/or snoring as herein noted.

Turning now to FIG. 7, apparatus 10f is shown that includes an appliance 26 that is non-circumferentially enclosed in structure. In other words, apparatus 10f, unlike apparatus 10a-10e, includes spaced apart end portions 27 defining a gap 32, and a closed or intermediate portion 34 between the ends portions 27. The end portions 27 may be rounded, as shown, or may have other desired shapes.

More specifically, the appliance 26 may be described as a substantially C-shaped member 35 defined by a pair of resilient, flexible wire struts 36a and 36b connected at the end portions 27 to define an enclosed, endless loop. The struts 36a and 36b may have any suitable transverse cross-section, for example, a circular, oval, rounded, flattened or other transverse cross-section.

In this particular embodiment, the C-shaped member 35 is formed from a wire or ribbon that forms a continuous loop as shown, defining an open interior space 38.

Still referring to FIG. 7, the appliance 26 is structured to be positioned within the oropharyngeal region with the end portions 27 bearing against and providing an opening force against the lateral walls of the oropharyngeal region. It is contemplated that the apparatus 10f may be alternatively positioned such that the appliance 34 rests substantially within or entirely within the valecullar space and presses against the base of the tongue along closed portion 34.

Upon contraction of the oropharyngeal region, for example, during swallowing, the end portions 27 will be temporarily forced toward one another by the muscles in the oropharyngeal region, and may or may not overlap or contact one another. The flexibility and relative spacing of the struts 36a and 36b allow the appliance 34 to contract and expand in the vertical direction as necessary, for example in conjunction with peristalsis of the pharyngeal walls upon swallowing.

Each of the embodiments of implants 10f-10j may be formed from highly elastic, biocompatible materials. For example, each of the implants 10f-10j may be formed from an elastic or a super-elastic material, e.g., a nickel titanium (NiTi) alloy, such as the alloy known as Nitinol.

For general background purposes, a description of the benefits of Nitinol follows that may applied to the apparatus and/or methods described herein. Additional details of this alloy can be obtained from readily available sources and/or will be known to those of skill in the art.

Nickel titanium (also known as Nitinol) is in the class of materials known as shape memory alloys. A thermoelastic martensitic phase transformation in the material is responsible for its extraordinary properties. These properties include the shape memory effect, super-elasticity, and high damping capability.

Nitinol has the ability to absorb large amounts of strain energy and release it as the applied strain is removed. Nitinol also has excellent torqueability and kink resistance, which is a useful feature for the apparatus and methods described herein due to the dynamic nature of the oropharyngeal and hypopharyngeal regions. Advantageously, super-elastic Nitinol alloys provide a substantially constant force over a large strain range.

The present apparatus may be formed from a Nitinol material with a ratio of the two constituents, nickel and titanium, at about fifty percent (50%) atomic percent each (e.g., about fifty five percent (55%) percent by weight of nickel).

The properties of Nitinol may be modified by changes in alloy composition, mechanical working, and heat treatment, as known to those of ordinary skill in the art. The specific alloy used in the apparatus described herein may be selected mainly for its super-elastic effect rather than its shape memory effect, however, temperature activated shape memory may also be used to control the bias or shape of the apparatus, e.g., upon being exposed to body temperatures within a patient.

Super-elastic Nitinol alloys may be used in the apparatus described herein to take advantage of a stress-induced martensitic transformation in order to achieve extreme amounts of flexibility and kink resistance. It is known that an alloy of nickel and titanium may behave super-elastically if its Active $A_f$ temperature (the temperature above which the material has undergone substantial transformation from its martensitic to its austenitic state) is just below the use temperature. For example, alloys that are intended to be super-elastic at room temperature are generally produced with their Active $A_f$ temperatures just below room temperature in the range of about zero to about twenty degrees Celsius (0-20° C.). A super-elastic material will not be super-elastic at all temperatures, but will exhibit good super-elastic properties in a temperature window extending from the Active $A_f$ temperature up to a temperature that is about fifty degrees Celsius (50° C.) above Active $A_f$. Therefore, a material with an Active $A_f$ of about fifteen degrees Celsius (15° C.) will exhibit good super-elasticity up to about sixty five degrees Celsius (65° C.), which means that the material will exhibit good super-elasticity at both ambient or room temperature and body temperature (37° C.).

Nitinol is a useful material for the apparatus described herein also due to its excellent biocompatibility, very high corrosion resistance, and excellent cytocompatibility. In addition, the nickel in nickel/titanium alloy is chemically joined to the titanium in a strong intermetallic bond, so the risk of reaction, even in patients with nickel sensitivity, is extremely low. In addition, Nitinol is not considered a fibrosis-inducing material. Additional details on nickel titanium alloys are known to those of ordinary skill in the art and are provided, for example, in U.S. Pat. No. 6,306,141 to Jervis, the entire disclosure of which is expressly incorporated by reference herein.

FIGS. 8-10 show alternative embodiments of implants similar to the embodiment shown in FIG. 7 in that the appliance is non-circumferentially enclosed as defined elsewhere herein.

More specifically, referring to FIG. 8, an apparatus 10g is shown that generally includes a cuff-shaped appliance 50. Like appliance 26, appliance 50 includes spaced apart end portions 27g defining a gap 32g, and closed portion 34g. A substantial distinction between apparatus 10g and apparatus 10f is that apparatus 10g includes relatively wide, opposing outer peripheral portions 56a and 56b, that define flattened bands, rather than struts 36a and 36b. The outer peripheral portions 56a and 56b define an open interior space 58. Relative to apparatus 10f, this particular design generally allows greater surface contact with oropharyngeal tissues as well as greater hoop strength or opening pressure.

FIG. 9 shows an apparatus 10h including a cuff-shaped appliance 60 similar to appliance 50 for accommodating a patient with different needs, for example, a patient having a longer, more narrow oropharyngeal region. Appliance 60 includes spaced apart end portions 27h defining a gap 32h and closed portion 34h.

FIG. 10 shows another apparatus 10i generally similar to the embodiment shown in FIG. 8. A significant distinction between apparatus 10i and apparatus 10g is that the apparatus 10i includes a mesh, braid, knit, or woven structure, which may provide increased flexibility and/or facilitate natural, non-fibrotic, tissue ingrowth to restrict or prevent migration of the apparatus 10i. For example, the appliance 64 includes an outer peripheral portion 66 made of a woven mesh wire for example, defining an interior space 68.

FIG. 11 shows yet another apparatus 10j, including a non-circumferential cuff-shaped appliance 82 having spaced apart end portions 27j defining a gap 32j. A significant distinction between apparatus 10j and apparatus 10g is that appliance 82 does not include interior space 58, but is instead substantially solid as shown. In addition, appliance 82 may include one or more through apertures 87 for facilitating natural, non-fibrotic, tissue ingrowth through the appliance 82.

FIGS. 12-21 show various embodiments of implants that are generally planar when in a resting or non-deployed state, for example, when the implant is located outside of the oropharyngeal region of a patient in a rest position. Except as expressly described herein, each of the apparatus 10k, 10m, 10n, 10p and 10q, 10s, 10t, 10u, 10v and 10w shown in FIGS. 12-21 respectively, may be constructed similar to apparatus 10 and is structured, unless otherwise noted herein, to be utilized for the treatment of sleep apnea and/or snoring as described elsewhere herein.

Figure 12:
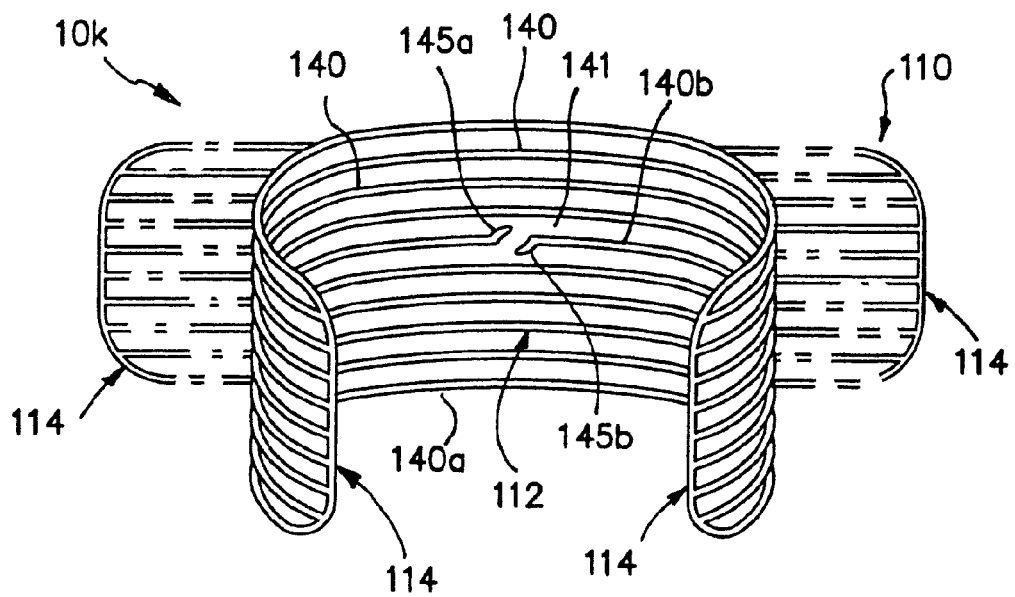
FIG. 12 is a perspective view of an alternate embodiment of an implant including a flat flexible member including spaced apart struts extending between rounded end portions.

Turning now to FIG. 12, apparatus 10k generally includes an appliance 110 having a flat or substantially planar configuration (represented by phantom lines) that is flexible to achieve an arched or curved configuration (shown in solid line). Like the embodiments shown in FIGS. 7-11, the apparatus 10k defines a non-circumferential configuration when in the deployed state. Stated differently, the apparatus 10k may be biased to the substantially planar configuration, but may be sufficiently resilient and/or flexible to be directed to the curved configuration, e.g., to allow delivery and/or implantation within the oropharyngeal region of a patient.

More particularly, as shown, the appliance 110 includes a body portion 112 and end portions 114 spaced apart by the body portion 112. The appliance 110 may be in any suitable form, such as, for example, a substantially rectangular form (shown in FIG. 12), a substantially circular form, a substantially oblong form, a substantially oval form or a substantially elliptical form or the like configuration. When located in the oropharyngeal region, the appliance 110 is structured to exert a sufficient force, e.g., a sufficient substantially constant radial force, on the oropharyngeal region, particularly against the lateral walls of the oropharyngeal region, to maintain or cause the airway passing through the region to be patent, so that it is substantially open or unobstructed.

The appliance 110 is structured to take on a deployed configuration when located within the oropharyngeal region such that the end portions 114 are spaced apart from each other by other than the body portion 112. For example, the end portions 114 may be spaced apart by the epiglottis or a portion of the anterior or posterior wall of the oropharyngeal region. The apparatus 110 is structured to be sufficiently resilient and flexible to allow for normal dynamic movement or motion of the oropharyngeal region with little or no loss in desirable properties, such as hoop strength and the like, over an extended period of wear.

Advantageously, the apparatus 10k may be formed entirely from a unitary flat sheet of material that is laser cut into the desired configuration. Using a flat elastic or super-elastic sheet of material or a sheet pre-curved to a diameter larger than that of the oropharyngeal region of the human or animal, the apparatus 10k, once implanted into the oropharyngeal region, applies substantially continuous opening pressure to the oropharyngeal walls, for example, the lateral walls of the oropharyngeal region.

Appliance 110 may have a longitudinal length (from one end portion 114 to the other end portion 114) between about forty millimeters (40 mm) and about ninety millimeters (90 mm) in the substantially flat configuration, and a lateral height of between about ten millimeters (10 mm) and about fifty millimeters (50 mm). The dimensions of appliance 110 may be selected based on individual patient need. The appliance is designed such that the effective non-constrained diameter of the appliance, when deployed, is greater than about thirty two millimeters (32 mm).

Appliance 110 includes a plurality of flexible wire or ribbon struts 140, which may extend between the radiused end portions 114 extending along a substantial portion of the length of the appliance 110. For example, the appliance 110 may include between about two (2) and about fifty (50) struts or more, or between about six (6) and about twenty (20) struts, such as about ten (10) struts.

In the embodiment shown in FIG. 12, each of the struts 140 has a thickness (into the sheet) of about 0.005 inch and a width (parallel to the lateral height) of about 0.010 inch. This design has been found to provide the required flexibility and resiliency in at least three dimensions or directions of motion, and, in addition, twisting motion, without exhibiting significant fatigue over an extended period of wear/time in service requiring dynamic movement, such as in the oropharyngeal region.

The number, thickness, and/or width of the struts 140 may be varied to produce a desired opening pressure (e.g., hoop strength) on the base of the tongue or to reduce or increase the surface area of the struts 140 which are in contact with the oropharyngeal walls. This design also may allow improved vertical collapse/deformation of the oropharyngeal region, for example, allowing peristalsis type movement during swallowing.

When provided in an oropharyngeal region of a patient for the treatment of sleep apnea and/or snoring, the appliance 110 is curved with a convex surface pressing against the tissues to be supported, particularly the lateral walls of the oropharyngeal region and/or the base of the tongue.

The appliance 110 is structured to be self-expanding with a controlled length during such expansion. This may be achieved by suitable selection of super-elastic materials, such as Nitinol, and appropriate selection of strut length and other dimensions. The appliance 110 may also be structured to have a relatively atraumatic nature of all surfaces thereof and of the curved end portions. In addition, the appliance 110 may be structured to exhibit the ability to be delivered in a minimal diameter access manner by rolling the appliance 110 onto itself within a catheter, cannula, inserter tube, and the like.

The appliance 110 may be tailored to be effective in a variety of patients and in a variety of different body regions that may benefit from the consistent support provided by such an appliance. For example, the size and structure of the appliance 100 may be selected to accommodate a specific need. The amount of force provided by the appliance 100 may be modified by appropriate selection of the number of struts, width and/or thickness of struts, and/or surface area covered by the struts and/or the like factors. Generally, as the struts become thinner and take up less surface area, the appliance 110 may become more compliant and may move and/or flex with less radial force exerted thereby and/or may flex to a greater extent without permanent deformation. It is noted that a portion of appliance 110 may be modified such that it may function to anchor or secure the appliance in place. For example, an outer or peripheral strut 140a may be configured to achieve a "fluted" configuration (not shown). In some embodiments, although not shown, one or more of the struts may be shaped as wave forms or s-shapes. In yet other embodiments, although not shown, cushioned end members may be provided on the end portions 114 of the appliance 110 in order to enhance comfort and/or proper fit.

An optional feature of the apparatus 110 is shown at 141 for facilitating anchoring of the apparatus 10k in the given position. More specifically, at least one of the struts 140b may be configured to form barbed portions 145a and 145b for enhancing secure attachment of the appliance 110 to the posterior wall of the oropharyngeal region. It is also contemplated that other features or methods for securing the apparatus 10k in the given position may be provided. For example, surfaces of the apparatus 10k may be coated with a biologically compatible glue or adhesive.

Figure 13:
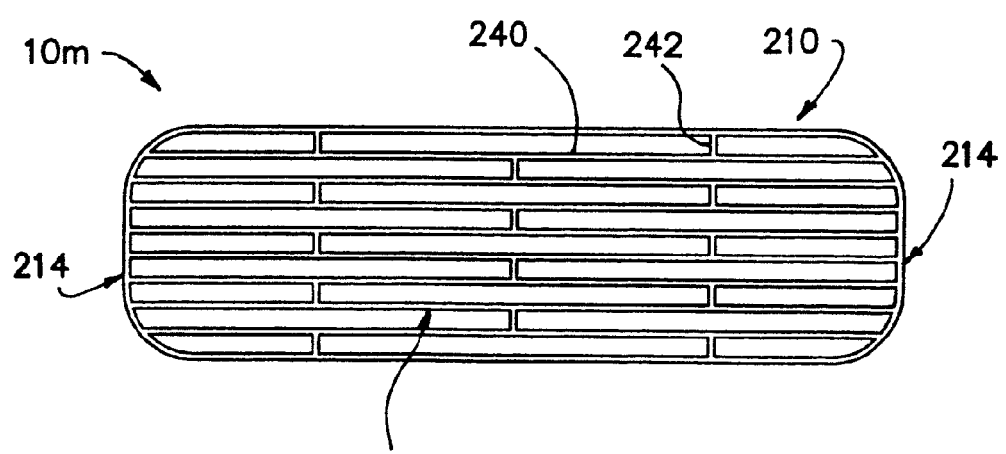
FIGS. 13-16 are plan views of other alternate embodiments of implants similar to the embodiment shown in FIG. 12.

FIG. 13 shows another apparatus 10m including appliance 210 for treating sleep apnea and/or snoring that may be generally similar to apparatus 10k. An additional feature shown on apparatus 10m is the addition of spacing portions 242, positioned and structured to maintain a spaced apart relationship between adjacent struts 240 when apparatus 10 is in the oropharyngeal region of a patient. Appliance 210 includes end portions 214 and body portion 212, also similar to the apparatus 10k.

Figure 14:
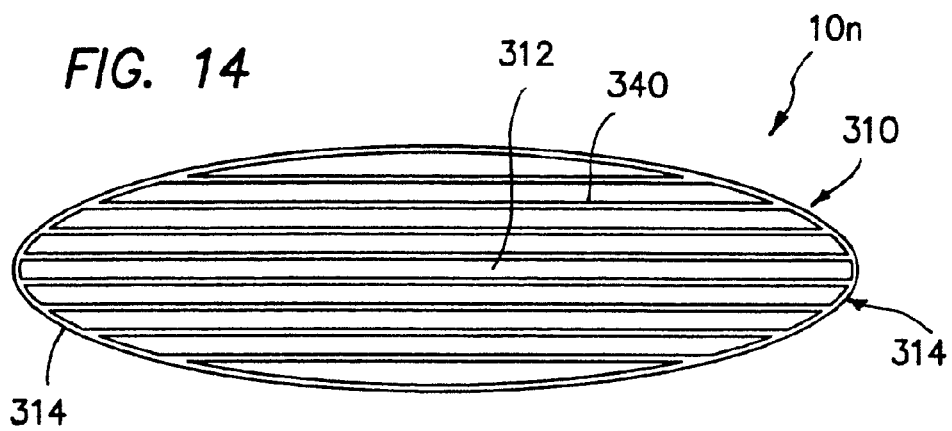
Figure 15:
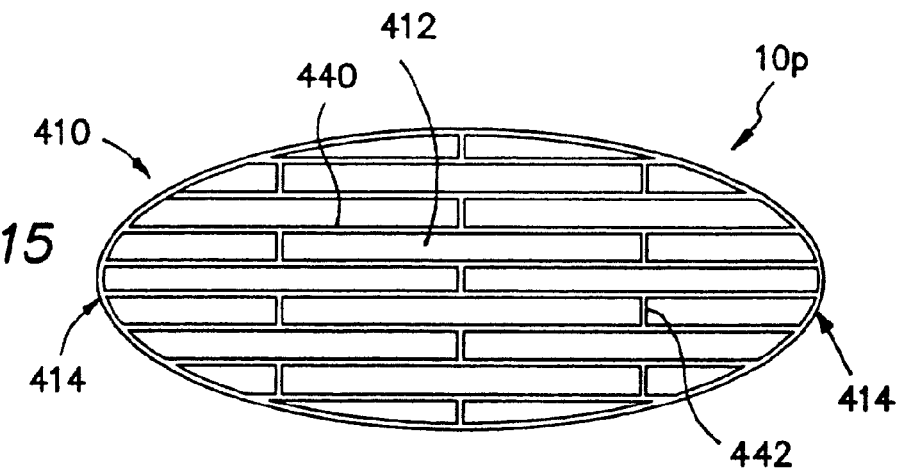

FIGS. 14 and 15 show apparatus 10n and 10p respectively, for treating sleep apnea and/or snoring that may also be similar to apparatus 10k and 10m, with the most significant distinction being that apparatus 10n and 10p are substantially oval or elliptical rather than rectangular in shape. Apparatus 10n generally includes appliance 310 including rounded end portions 314 joined by an intermediate body portion 312, and a plurality of spaced apart struts 340. Apparatus 10p generally includes appliance 410 including rounded end portions 414 joined by an intermediate body portion 412, and a plurality of spaced apart struts 440 and spacing portions 442.

Figure 16:
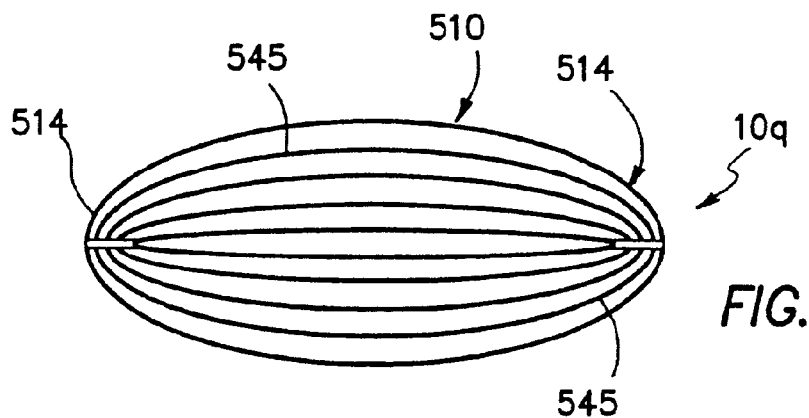

FIG. 16 shows yet another apparatus 10q for treating sleep apnea and/or snoring that includes an appliance 510 having a substantially elliptical shape and including a plurality of bowed or arched struts 545 that converge at end portions 514.

Turning now specifically to FIGS. 17-21, additional alternative embodiments of implants or stents are shown. Like the embodiments shown in FIGS. 12-16, these embodiments are typically planar in structure when at rest and not deployed in the oropharyngeal region of a patient. Alternatively, these embodiments may be biased to a curved configuration, e.g., having a radius of curvature larger than the oropharyngeal region. A significant distinction between the embodiments shown in FIGS. 12-16 and the alternative embodiments shown in FIGS. 17-21, is that the latter embodiments are each defined a single continuous loop.

Figure 17:
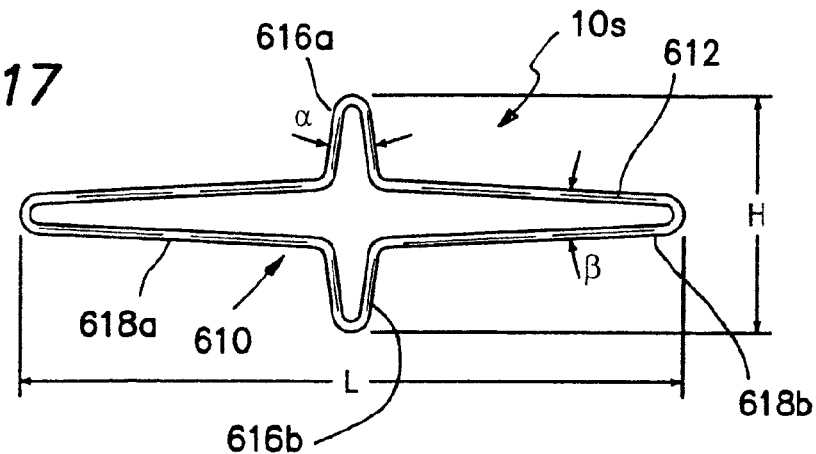
FIGS. 17-21 are plan views of various other alternative embodiments of implants including a single loop element.

More specifically, FIG. 17 shows an apparatus 10s for treating sleep apnea and/or snoring including a substantially cross-shaped appliance 610, defined by a single loop element 612. The appliance 610 may be made, for example, from 0.010 inch to 0.024 inch diameter Nitinol superelastic round wire or cut, e.g., photoetched from a single sheet of material, such as a sheet of a Nitinol superelastic alloy material having a sheet thickness of about 0.010 inch to about 0.100 inch. The appliance 610 may have a lateral height H along a vertical axis of about ten millimeters (10 mm) to about fifty millimeters (50 mm), and a longitudinal length L along a horizontal axis of about forty millimeters (40 mm) to about ninety millimeters (90 mm) allowing an effective non-constrained diameter of greater than about thirty two millimeters (32 mm). As shown, the cross-shaped appliance 610 is substantially symmetrical about its vertical and horizontal axes. Appliance 610 includes vertical portions 616a and 616b each defining an angle $\alpha$, and horizontal portions 618a and 618b each defining an angle $\beta$.

For purposes of example only, vertical portions 616a and 616b define a peak-to-peak measurement (i.e., height H) of about twenty five millimeters (25 mm), and horizontal portions 618a and 618b define a peak-to-peak measurement (i.e., length L) of about fifty millimeters (70 mm). Also for purposes of this specific example only, each of vertical portions 616a and 616b defines an angle $\alpha 0$ of about fifteen degrees (15°) and each of horizontal portions 618a and 618b defines an angle $\beta$ of about six degrees (6°).

Appliance 610 is structured to be placed in the oropharyngeal region in a position such that horizontal portions 618a and 618b rest against and provide support to the lateral walls of the oropharyngeal region. The vertical axis of the apparatus 610, generally defined by vertical portions 616a and 616b, are disposed against or adjacent the posterior wall of the oropharyngeal region.

Figure 18:
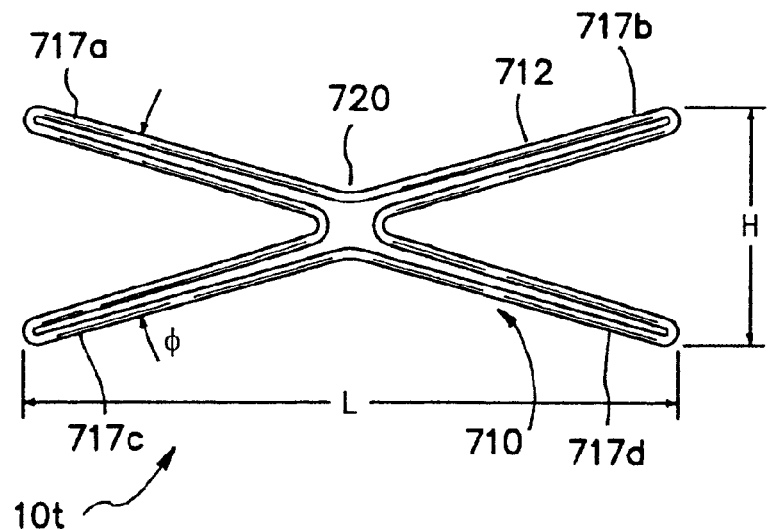

FIG. 18 shows yet another apparatus 10t for treating sleep apnea and/or snoring that may be similar to apparatus 10s in that it is defined by a single loop element 712 of round wire or cut from a single sheet of material, for example, a Nitinol alloy. A substantial distinction between apparatus 10s and apparatus 10t is that, rather than being a cross-shaped appliance 610, apparatus 10t includes a substantially X-shaped appliance 710 having a length L and a height H. Appliance 710 includes multiple leg portions 717a, 717b, 717c and 717d extending from a generally central region 720, wherein paired leg portions 717a and 717c and paired leg portions 717b and 717d, both define an angle $\phi$.

For purposes of this specific example only, appliance 710 has a length L of about fifty millimeters (50 mm) and a height H of about twenty five millimeters (25 mm), and angle $\phi$ is about thirty six degrees (36°).

Appliance 710 is structured to be placed in the oropharyngeal region in a position such that leg portions 717a, 717b, 717c and 717d rest against and provide support to the lateral walls of the oropharyngeal region, and the generally central portion 720 is disposed against or adjacent the posterior wall of the oropharyngeal region.

Figure 19:
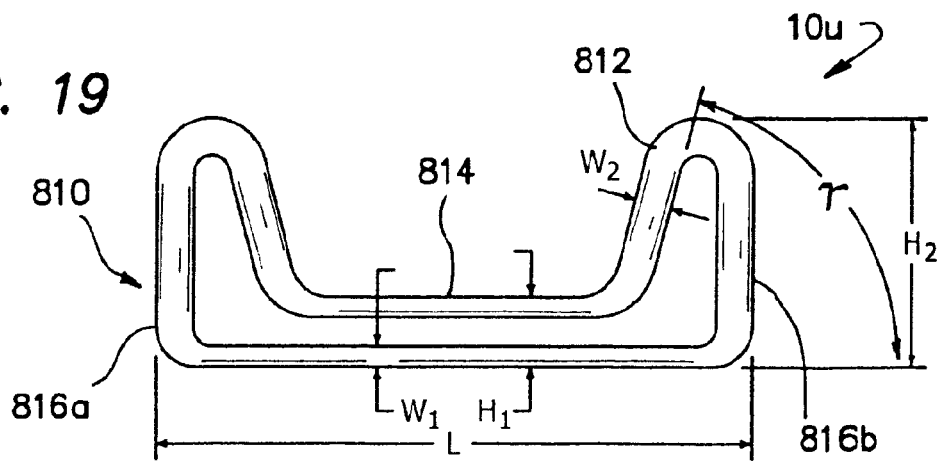

FIG. 19 shows yet another apparatus 10u for treating sleep apnea and/or snoring that may be similar to apparatus 10s in that it is defined by a single loop element 812 cut from a single sheet of material, for example, a Nitinol alloy. Apparatus 10u includes an appliance 810 having a relatively narrow, generally central body portion 814 (having height $H_1$) terminating at relatively wide end portions 816a and 816b (having height $H_2$), and a length L. End portions 816a and 816b define angle $\gamma$ as shown.

For purposes of this specific example only, appliance 810 may have a length L of about fifty millimeters (50 mm), a height $H_1$ of about ten millimeters (10 mm), a height $H_2$ of about thirty five millimeters (35 mm), and an angle $\gamma$ of about seventy five degrees (75°). Element 812 may have a width $W_1$ at generally central portion 814 and a width $W_2$ of about five millimeters (5 mm) at end portions 816a and 816b.

Appliance 810 is structured to be placed in the oropharyngeal region in a position such that end portions 816a and 816b rest against and provide support to the lateral walls of the oropharyngeal region, and the generally central body portion 814 is disposed against or adjacent the posterior wall of the oropharyngeal region.

Figure 20:
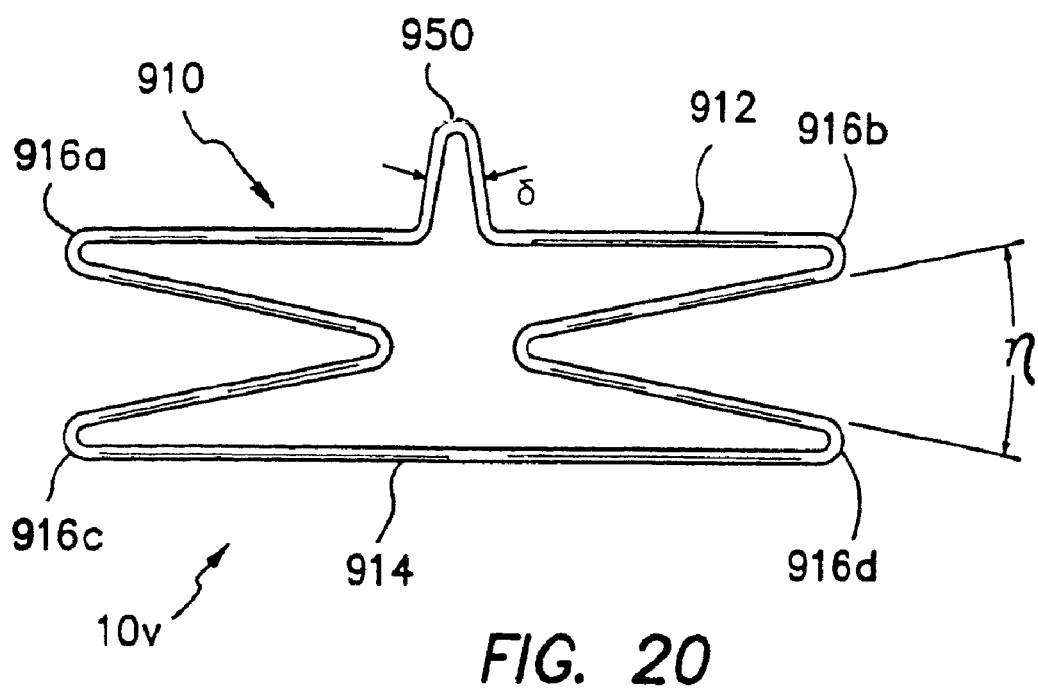

FIG. 20 shows yet another apparatus 10v for treating sleep apnea and/or snoring that includes an appliance 910 defined by an endless loop element 912, and including a generally central body portion 914, and multiple end portions 916a, 916b, 916c and 916d. As shown, adjacent end portions define an angle $\eta$. Appliance 910 further includes a vertical portion 950 that defines an angle $\delta$.

Appliance 910 is structured to be placed in the oropharyngeal region in a position such that multiple end portions 916a, 916b, 916c and 916d rest against and provide support to the lateral walls of the oropharyngeal region, and the generally central body portion 914 is disposed against or adjacent the posterior wall of the oropharyngeal region.

Figure 21:
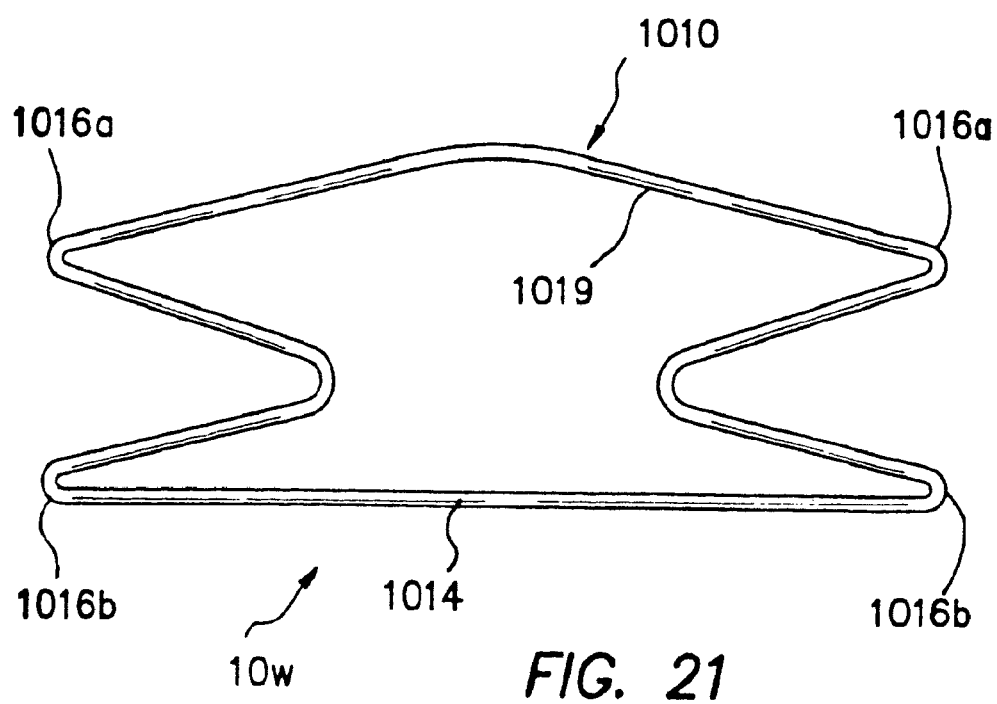

FIG. 21 shows yet another apparatus 10w for treating sleep apnea and/or snoring that includes an appliance 1010 that is somewhat similar to appliance 910 in that appliance 1010 includes a generally central body portion 1014 and multiple end portions 1016a, 1016b, 1016c and 1016d. Appliance 1010 has somewhat different proportions, including a relatively wide upper central portion 1019 that is configured to provide enhanced tissue support to portions of the posterior wall of the oropharyngeal region, relative to tissue support provided by appliance 910.

Figure 22:
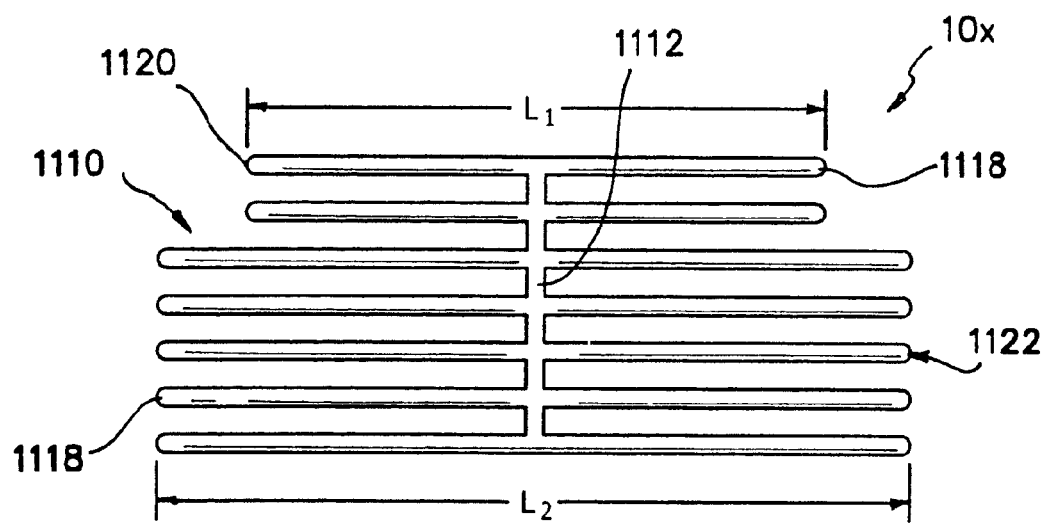
FIGS. 22-23 are plan views of yet other embodiments of implants.
Figure 23:
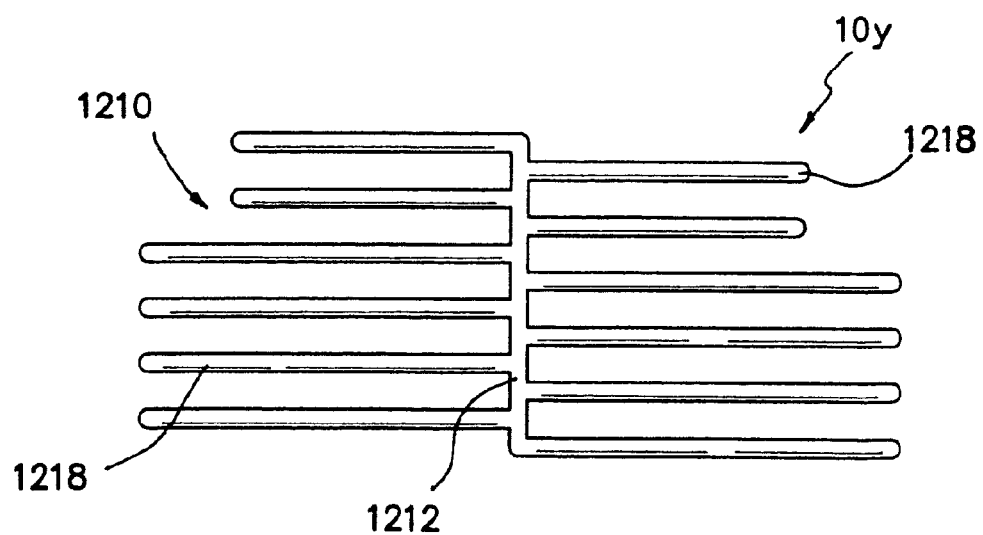

FIGS. 22-23 show other embodiments of implants or stents for treating sleep apnea and/or snoring. Like the embodiments shown in FIGS. 12-21, these embodiments are typically planar in structure or curved to a diameter in excess of thirty two millimeters (32 mm) when at rest and not deployed in the oropharyngeal region of a patient.

FIG. 22 shows an apparatus 10x including a substantially symmetrical appliance 1110 including a substantially linear body portion 1112 and a plurality of struts 1118 extending from the body portion 1112, for providing support to the oropharyngeal tissues. The number and length of struts 1118 may be selected based on a particular patient need or other parameters. For purposes of example only, appliance 1110 may have an upper portion 1120 having about two pairs of struts 1118 defining a tip to tip length $L_1$ of about forty two millimeters (42 mm), and a lower portion 1122 having about five pairs of struts 1118 defining a tip to tip length $L_2$ of about sixty two millimeters (62 mm).

FIG. 23 shows an apparatus 10y that is similar to apparatus 10x. The most significant distinction is that apparatus 10y includes an appliance 1210 including a body portion 1212 and struts 1218 that are offset from one another along body portion 1212.

Figure 24:
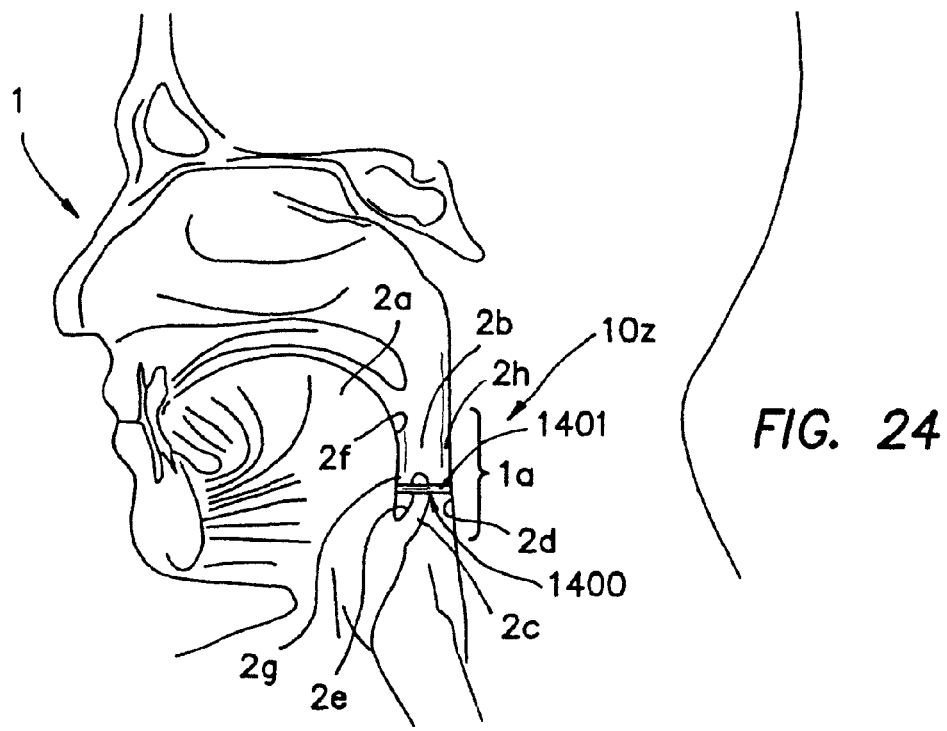
FIG. 24 is a cross-sectional view of a patient's head, showing a side view of an exemplary embodiment of an implant including an elongated element structured to be at least partially submucosally implanted in the oropharyngeal region of a patient.

Turning to FIG. 24, another embodiment of an apparatus 10z is shown that is generally similar to apparatus 10a through apparatus 10x in that apparatus 10z is structured to be effective in maintaining patency of the airway of a patient 1, for example, the oropharyngeal region 1a of a patient. However, apparatus 10z is specifically structured to be at least partially, and in some cases substantially entirely submucosally, implantable into the pharyngeal region, for example the oropharyngeal region, of the patient.

Figure 25:
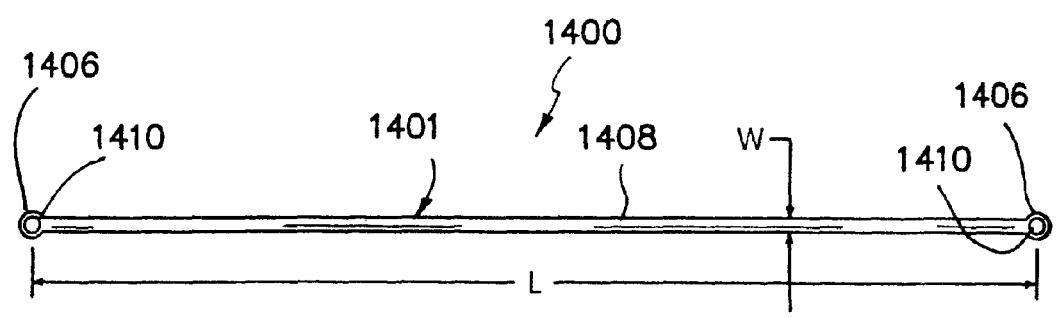
FIG. 25 is a plan view of the implant shown in FIG. 24.

Apparatus 10z, more clearly shown in FIG. 25, includes a single elongated element 1401 having end portions, for example, rounded end portions 1406 and a body portion 1408 extending or connected therebetween.

Figure 25A:
FIGS. 25A and 25B are cross-sectional views of alternative cross-sectional shapes for the implant shown in FIG. 25.
Figure 25B:
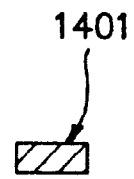

As shown, end portions 1406 are structured to facilitate implantation, for example, surgical implantation, of the element 1401. For example, end portions 1406 may include appropriately sized apertures 1410 for receiving suturing thread. The element 1401 may have a rounded cross-section such as shown in FIG. 25A, or a polygonal cross section, for example a rectangular cross section, such as shown in FIG. 25B.

Referring to FIG. 25, element 1401 may have a length L between about fifty millimeters (50 mm) and about seventy millimeters (70 mm) and a width W between about two millimeters (2 mm) or less and about six millimeters (6 mm). Dimensions of the appliance 1400 may be at least in part based upon, for example, the size or diameter of the patient's pharyngeal region and the specific portion of the pharyngeal region to be supported by the apparatus 10z. A typical area of support as mentioned elsewhere herein, is the area encompassing, at least, a portion of one or more of the lateral walls of the oropharyngeal region.

Appliance 1400 may be formed from Nitinol or other suitable, flexible, elastic biocompatible material, e.g., as discussed elsewhere herein.

Advantageously, the element 1401 is designed to be surgically implantable in the pharyngeal region, at least partially circumscribing the region, and at least partially or substantially entirely, beneath the mucosal layer thereof The appliance 1400 may also be at least partially sutured to the pharyngeal tissues, for example, at end portions 1401a of the element 1401, and/or secured to the oropharyngeal tissues by means of a biocompatible adhesive.

Figure 26:
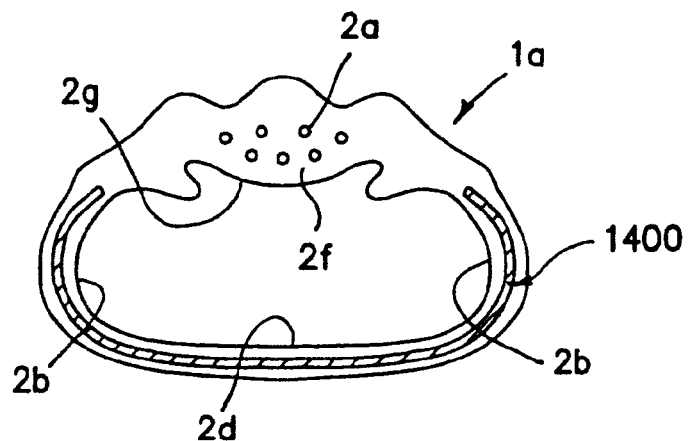
FIGS. 26-28 are cross-sectional views of the oropharyngeal region of a patient, showing various implants submucosally implanted therein.

Turning now to FIG. 26, appliance 1400 is shown sized to be placed at least partially circumscribing an interior hollow passage (representing a cross-section of the airway of the patient) defining the pharyngeal region. This view (as well as views shown in FIG. 27 and FIG. 28) is a simplified representation of a cross-section of the oropharyngeal region 1a, with posterior wall 2d and anterior wall 2g, (which includes the base 2f of the tongue 2a) and opposing right and left lateral walls 2b. This placement of appliance 1400 is effective in providing support to the lateral walls 2b of the oropharyngeal region 1a. The appliance 1400 is shown substantially entirely submucosally implanted.

Figure 27:
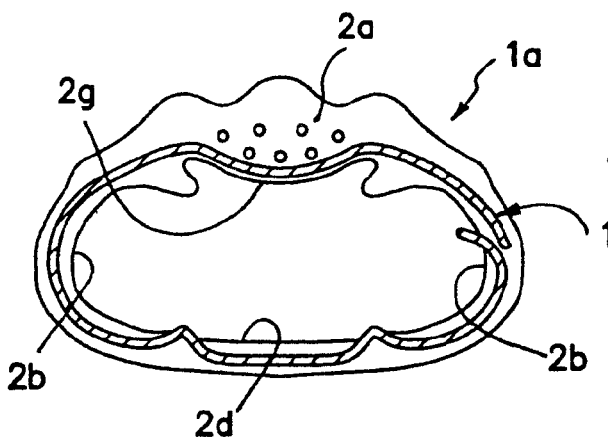

Turning now to FIG. 27, appliance 1400 is shown sized to be placed circumscribing, at least one full circumference of, the interior hollow space defined by the pharyngeal region. In this case, the appliance 1400 is sized to traverse the base 2f of the tongue 2a, for example, beneath the mucosal tissue thereof. The appliance 1400 is shown partially submucosally implanted.

Figure 24A:
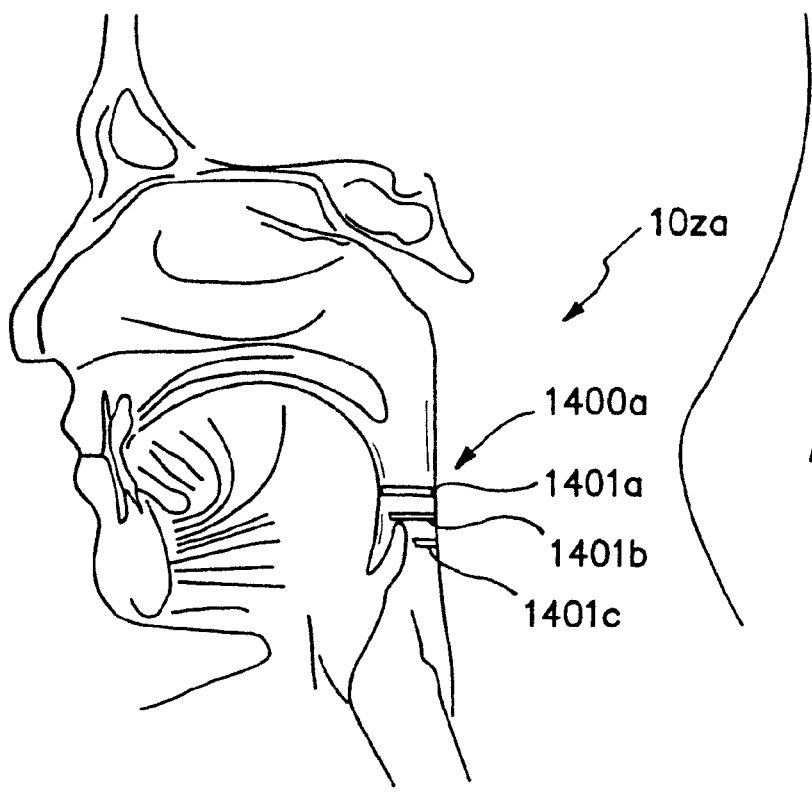
FIG. 24A is a cross-sectional view of a patient's head, showing an alternative embodiment an implant similar to the embodiment shown in FIG. 24, including multiple, spaced apart elongated elements at least partially submucosally implanted within the oropharyngeal region of the patient.

FIG. 24A shows another apparatus, generally at 10za that is substantially similar to apparatus 10z, except that apparatus 10za includes an appliance 1400a including a plurality of elongated, spaced apart elements, for example at least two, or three, or even more spaced apart elements 1401a, 1401b, and 1401c, depending upon the specific needs of a particular patient. Except as indicated elsewhere herein, it is to be appreciated that elements 1401a, 1401b and 1401c are structured to be placed, for example, at least partially submucosally, implanted in a manner as described hereinabove with respect to element 1401.

Each element 1401a, 1401b, and 1401c may be substantially, entirely independent, or unitary, in structure with respect to each other element 1401a, 1401b, and 1401c. Alternatively, the multiple elements 1401a, 1401b, and 1401c may be secured to each other by suitable means, for example, suturing, wire, ribbon or the like, for substantially maintaining the spaced apart relationship between the elements 1401a, 1401b, 1401c when the elements 1401a, 1401b, 1401c are positioned within and secured to the oropharyngeal region.

In another embodiment, a method is provided for maintaining patency of an oropharyngeal region. Particularly, the method may include at least partially submucosally placing at least one elongated element within the pharyngeal region, for example, within the oropharyngeal region in one or more strategic locations, wherein the placement thereof may cause the region to be stiffened or strengthened against collapse during natural sleep.

Figure 28:
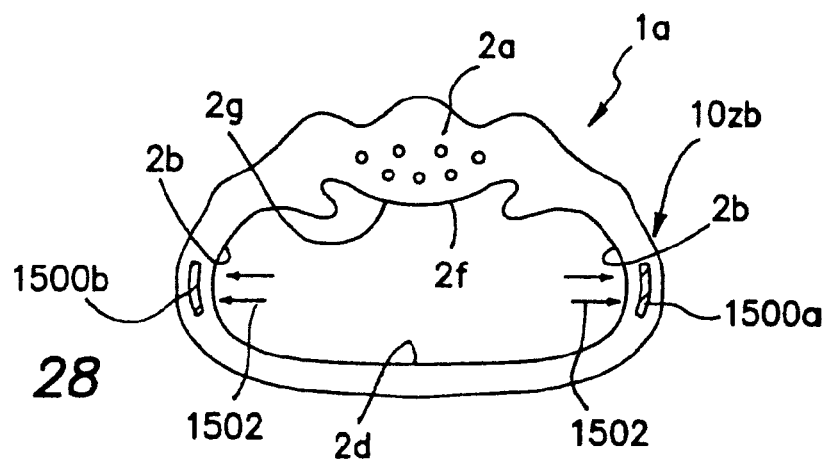

To illustrate another optional feature of the apparatus described herein, FIG. 28 shows a simplified view of the oropharyngeal region 1a of a patient, having apparatus 10zb submucosally implanted therein. Apparatus 10zb includes one or more magnetic components 1500a and 1500b, structured and designed to be effective to provide a magnetic field useful for providing gentle, substantially constant and continuous resistance against collapse of the pharyngeal walls, particularly the lateral walls 2b of the oropharyngeal region 1a, for example during natural sleep, while allowing substantially normal functioning of the pharyngeal region, for example during swallowing.

In the example shown, the two magnetic components 1500a, 1500b are strategically placed within the oropharyngeal region 1a such that like magnetic poles (i.e., repellant magnetic poles) are positioned substantially facing one another to create a magnetically repellant force therebetween (indicated in simplified form by arrows 1502). The repellant force caused by the strategically placed magnetic components 1500a and 1500b is effective for providing an opening force within the oropharyngeal region, thereby maintaining patency of the region during natural sleep while still allowing constriction of the region during swallowing.

FIG. 29A through FIG. 29E show various views of another embodiment of an apparatus 2010, which generally includes an implant, stent, or appliance 2012. Optionally, the apparatus 2010 may include other features, such as the needle 2030 and suture 2032 shown in FIG. 29G or other delivery device (not shown), as described elsewhere herein.

As shown in FIG. 29B, the appliance 2012 has a generally "bow-tie" shape in a generally vertical direction, i.e., along a vertical axis 2016, as best seen in FIG. 29B. In addition, the apparatus 2012 has a curved shape in a generally horizontal plane that intersects the vertical axis 2016, as best seen in FIG. 29C. The appliance 2012 generally includes a vertically narrow central region 2018 flanked by vertically wide or broadened first and second regions 2020, i.e., generally defining the "bow-tie" shape. As shown in FIG. 29C, within the horizontal plane, the central region 2018 may curve around vertical axis 2016, and the broadened regions 2020 may curve away from the vertical axis 2016. Alternatively, as shown in FIGS. 31A-31D, the central region 2018" and the broadened regions 2020" may both curve around the vertical axis 2016," e.g., in a substantially continuous "C" shaped curve, which may be a portion of a circle or ellipse.

Optionally, one or both broadened regions 2020 may terminate in a rounded tip 2021, e.g., that may be vertically narrower than the broadened regions 2020 and/or vertically narrower than the central region 2018. In addition or alternatively, the tip(s) 2021 may curve relative to the broadened regions 2020, e.g., curving away from the vertical axis 2016 within the horizontal plane. As shown, the tips 2021 curve within the horizontal plane at a tighter radius of curvature than the broadened regions 2020, as shown in FIG. 29C.

As best seen in FIG. 29B, the appliance 2012 may be formed from a unitary, continuous, closed loop element 2014 surrounding and/or substantially enclosing an open area 2022, e.g., made from a round, square, or other cross-section loop of wire loop. For example, a wire may be bent or otherwise formed into the desired shape and the ends may be coupled to one another, e.g., butt welded or soldered, sonic welded, heat sealed, fused, bonded with adhesive, crimped within a collar, captured within a section of shrink tubing, and the like, depending upon the material of the wire used. The wire may be heat treated or otherwise treated to program in the desired shape and/or impart the desired elasticity and/or other properties into the resulting apparatus 2010. Alternatively, the apparatus 2010 may be formed from a sheet of material, e.g., by laser cutting, machining, etching, and the like, before or after programming a desired shape into the sheet.

Figure 29E:
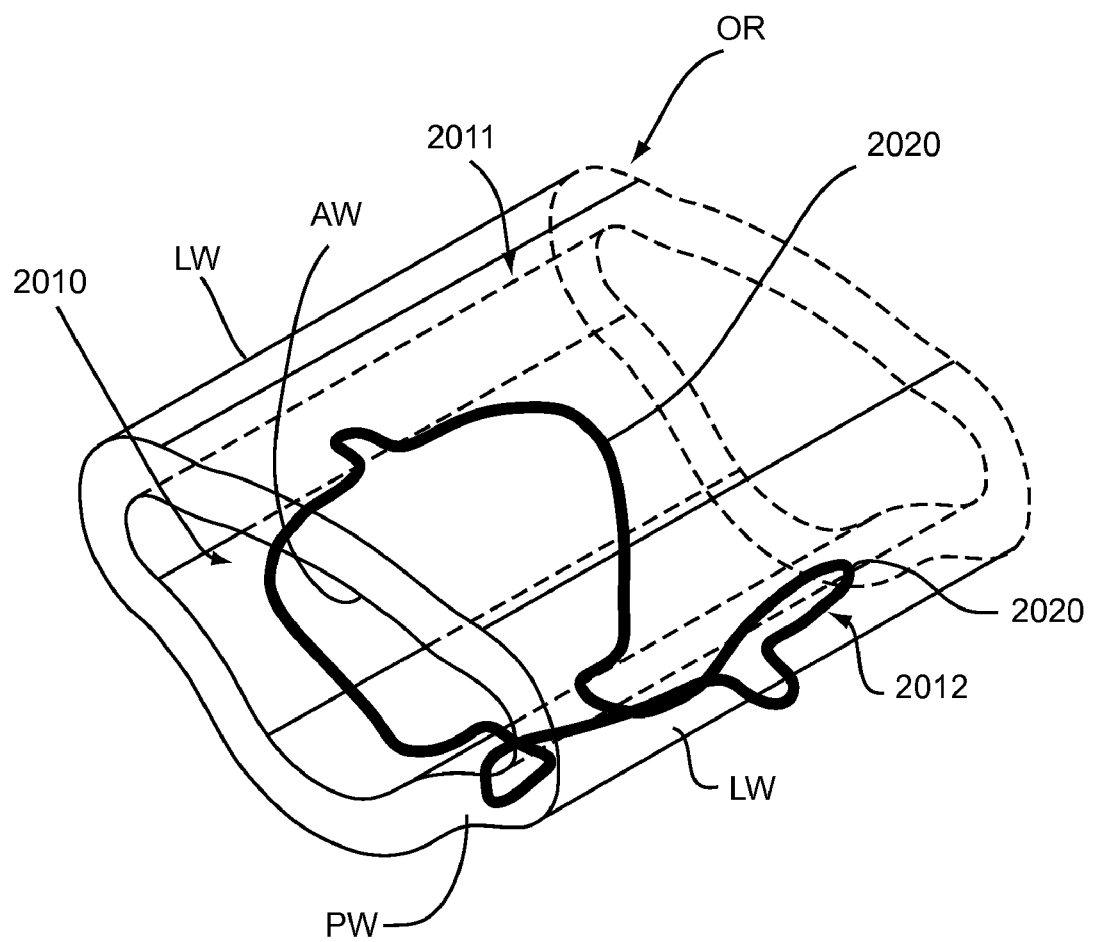
FIG. 29E is a perspective view of the oropharyngeal region of a patient, showing the implant of FIGS. 29A-29D placed in the posterior and lateral walls of the region.

Turning to FIG. 29E, the apparatus 2010 may be structured to be surgically placed in a oropharyngeal region of a patient, generally designated as "OR." As can be seen in FIG. 29E, a simplified perspective view of the oropharyngeal region OR is shown, showing posterior wall PW, anterior wall AW, and lateral walls LW of the oropharyngeal region OR.

It can be appreciated from FIG. 29E that the broadened regions 2020 of the appliance 2012 arc outwardly from the generally central region 2018. Broadened regions 2020 may be shaped to generally conform to the natural contours of the oropharynx and/or to provide support thereto. When properly implanted, the broadened regions 2020 may be located beneath the mucosal layer of the posterior and/or lateral oropharyngeal walls or may simply abut the posterior and/or later oropharyngeal walls, as described elsewhere herein. Optionally, the narrow tips 2021 may have an enhanced bias relative to the broadened regions 2020, e.g., to enhance securing the appliance 2010 within the oropharyngeal region OR.

As best seen in FIG. 29B, the portions of the wire defining the broadened regions 2020 may extend at least partially laterally or diagonally relative to the longitudinal axis 2016. For example, the broadened regions 2020 may include curved portions extending from the tips 2021 diagonally relative to the vertical axis 2016. Such lateral portions may facilitate collapsing the broadened regions 2020 when the appliance 2012 is directed through a relatively small opening, such as a puncture through a ligament or other tissue structure, as described elsewhere herein.

The appliance 2012 may be sufficiently resilient and/or elastic such that the broadened regions 2020 may be collapsed vertically from their relaxed state (shown in FIG. 29B), e.g., when directed through a relatively small opening, yet biased to resiliently expand back towards the relaxed state after passing through the opening. The portion of the open area 2022 within the broadened regions 2020 may define a relatively large surface area, which may enhance apposition between the broadened regions 2020 and adjacent tissue, as described elsewhere herein.

Alternatively, the broadened regions 2020 may have different shapes than that shown. For example, the broadened regions may have diamond shapes in the relaxed state, e.g., extending between the central region and the narrow tips. In another alternative, the broadened regions may have circular or elliptical shapes, e.g., with or without the narrow tips. In still another alternative, the broadened regions may have generally triangular shapes, e.g., within one of the apices of the triangles oriented towards the central region and bases of the triangles defining ends of the appliance. In yet another alternative, the broadened regions may have generally rectangular, square, or other geometric shapes that are larger than the narrower central region.

Figure 29F:
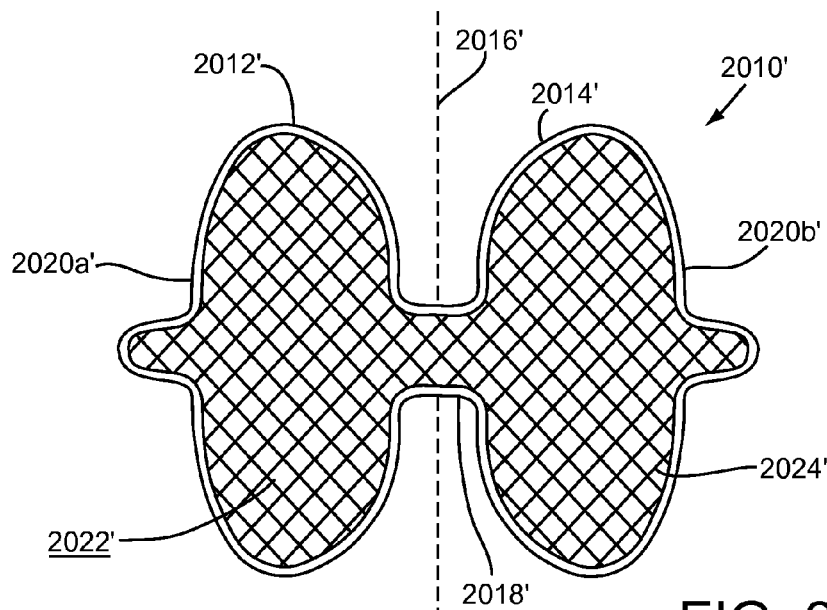
FIG. 29F is a front view of an alternative embodiment of the implant of FIGS. 29A-29D, including a mesh fabric covering central areas of the implant, e.g., to improve support/or and facilitate stability.

Optionally, as shown in FIG. 29F, the open area 2022' of the appliance 2010' may be covered, for example, with a mesh, fabric, braid, membrane or other material. The material may include any of the material described elsewhere herein, e.g., such as those from which the appliance 2010' may be formed, or other materials, such as Dacron® and the like. Such material may enhance tissue ingrowth after implantation. Optionally, the material may be coated or otherwise provided with therapeutic or other compounds, e.g., to enhance tissue ingrowth, healing, and the like.

Figure 29G:
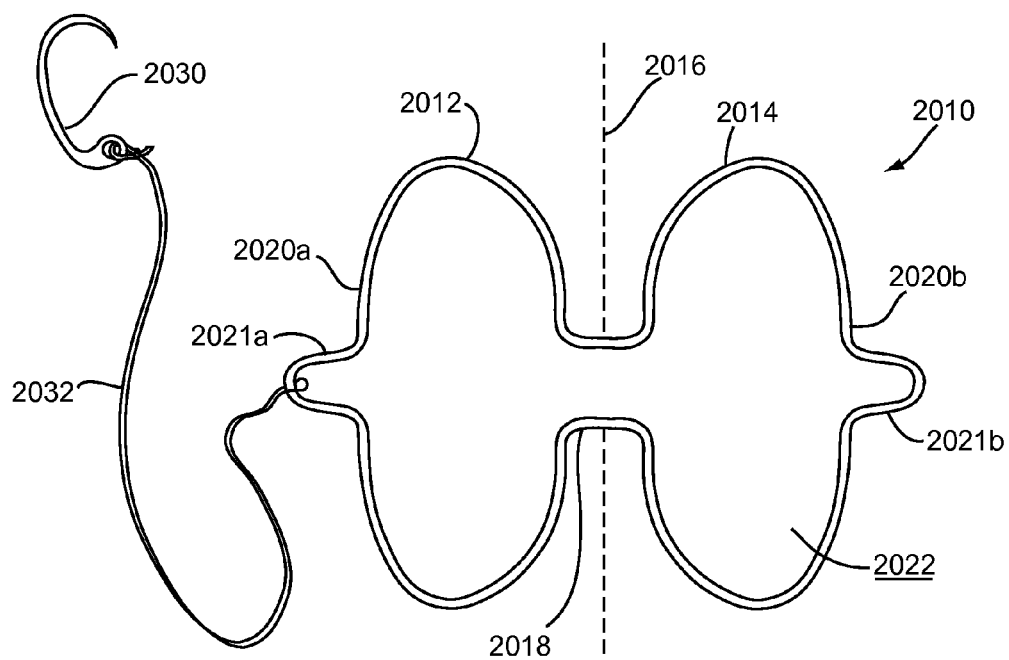
FIG. 29G is a front view of a system for implantation within the oropharyngeal region of a patient, including the implant of FIGS. 29A-29E.

Optionally, as shown in FIG. 29G, a needle 2030 may be coupled to one of the narrow tips 2021, e.g., by a suture or other filament 2032 to provide a system for delivering the appliance 2010 into the oropharyngeal region OR (not shown, see FIG. 29F). As described further below, the needle 2030 may have a "U" or other shape to facilitate introduction through a ligament or other tissue structure adjacent the oropharyngeal region OR or other implantation site. The suture 2032 may be a double suture looped through the narrow tip 2021 such that, the suture 2032 may be cut or otherwise severed at one location to allow the suture 2032 and needle 2030 to be removed, e.g., after implanting the appliance 2010, as described further below.

Alternatively, other delivery devices (not shown) may be provided for facilitating delivery of the appliance 2012, e.g., depending upon the target location for implantation. For example, a catheter, cannula, or other tubular member (not shown) may be provided within which the appliance 2012 may be loaded, e.g., after manufacturing or immediately before implantation. For example, a suture, tool, and the like (also not shown) may be coupled to one of the narrow tips 2021 and used to pull the appliance 2012 into a lumen of a first end of a cannula, the broadened regions 2020 being resiliently compressed as the appliance 2012 is pulled therein. As the appliance 2012 is pulled into the cannula, the appliance 2012 may also be substantially straightened within the horizontal plane. The appliance 2012 may be deployable from the cannula using a plunger or other pusher device within the cannula, e.g., adjacent the narrow tip 2021 used to pull the appliance 2012 into the cannula. Alternatively, another suture, tool, and the like may be coupled to the narrow tip 2021 closest to the first end of the cannula and used to pull the appliance 2012 back out of the cannula, whereupon the broadened regions 2020 may resiliently expand.

Referring now to FIGS. 30A-30D, a generally "bowtie" shaped appliance 2012, such as those shown in FIGS. 29A-29F, may be designed to be surgically implanted into an oropharyngeal region OR of a patient using direct visualization and a curved, e.g., "U" shaped, needle 2030 and suture 2032, such as that shown in FIG. 29G. The suture 2032 may be tied to or otherwise coupled to either narrow tip 2021 of the appliance 2012, e.g., by looping the suture 2032 around the wire of the appliance 2012 and through an eye of the needle 2030, and securing the ends together. Alternatively, one end of a suture may be attached to the narrow tip 2021 using a knot, for example, one that is tapered and will easily come apart when cut (e.g. a "fisherman's" knot), and the other end of a suture may be attached to the needle 2030, e.g., also by knotting.

During use, the needle 2030 (not shown, see FIG. 29G) may be introduced into the posterior wall of the oropharynx, for example at about one to four centimeters (1-4 cm) above the epiglottis (not shown), and approximately 0.2 cm lateral to the centerline CL. The needle 2030 is then pushed through or behind the anterior longitudinal ligament (ALL) located anterior to the spine 2019 so that it emerges from the tissue at the same distance above the epiglottis and approximately 0.2 cm from the centerline on the side opposite that where the needle was introduced, thereby creating passage or opening OP. The needle 2030 is then pulled out of the tissue along with sufficient length of suture 2032 to allow it to be grasped and used to pull the appliance 2012 through or behind the ligament (ALL). Significant resistance on the needle and suture as they are pulled through the tissue provides assurance that they have passed through or behind the ligament (ALL).

Figures 30A, 30B:
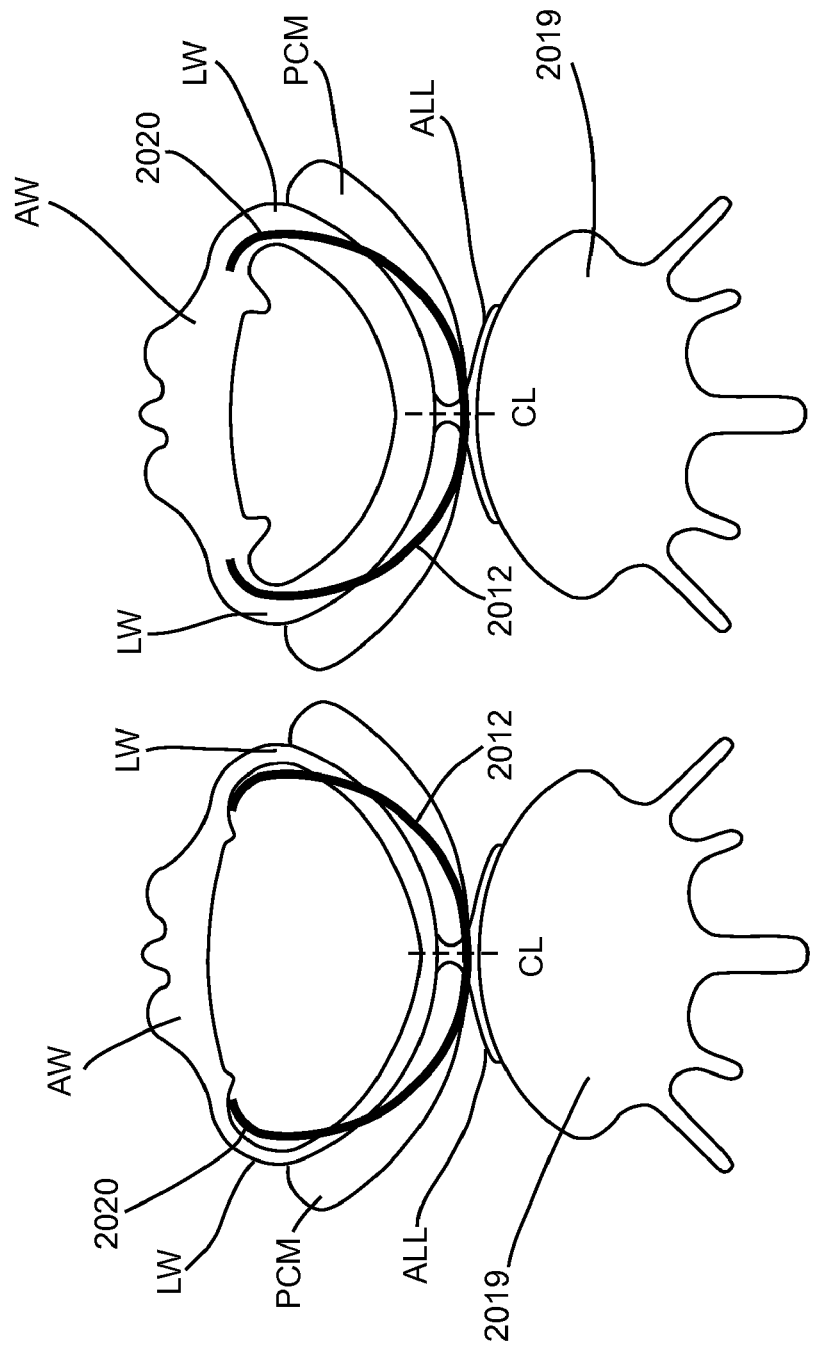
FIGS. 30A and 30B are cross-sectional views of a patient, showing an implant located within the oropharyngeal region in the delivered and final positions, respectively.
Figure 30C:
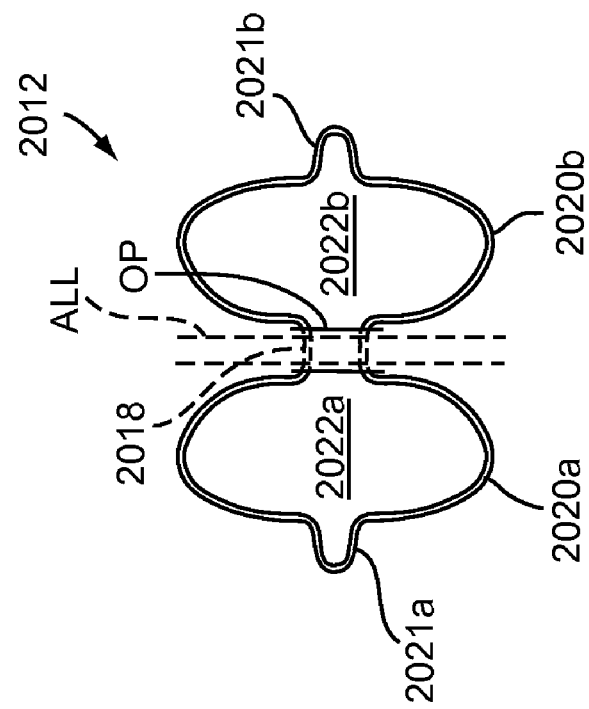
FIGS. 30C and 30D are details of the oropharyngeal region of FIGS. 30A and 30B, showing an implant being advanced through or behind the anterior longitudinal ligament.
Figure 30D:
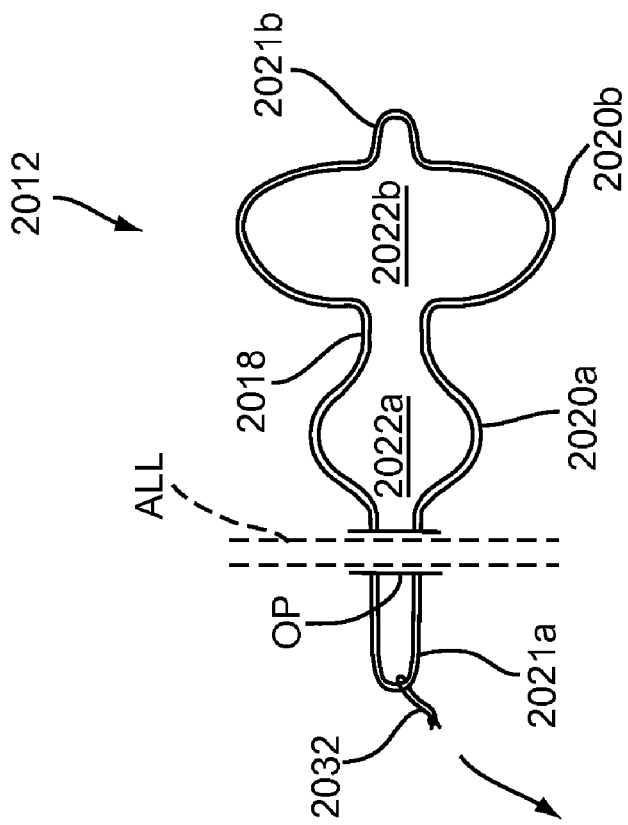
Figure 31A:
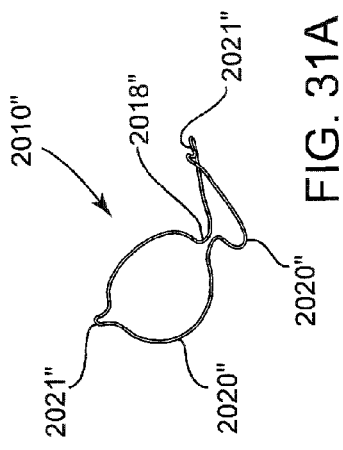
FIGS. 31A-31D are perspective, front, top, and side views, respectively, of another alternative embodiment of an implant for treating sleep apnea, snoring, and/or other breathing disorders, similar to the embodiment of FIGS. 29A-29E.
Figure 31D:
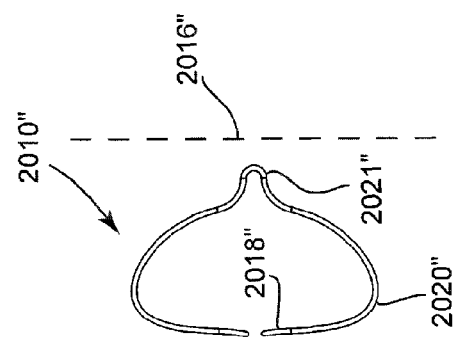
Figure 31C:
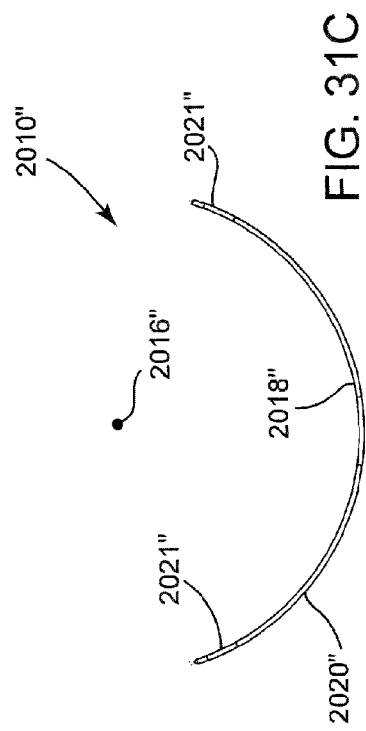
Figure 31B:
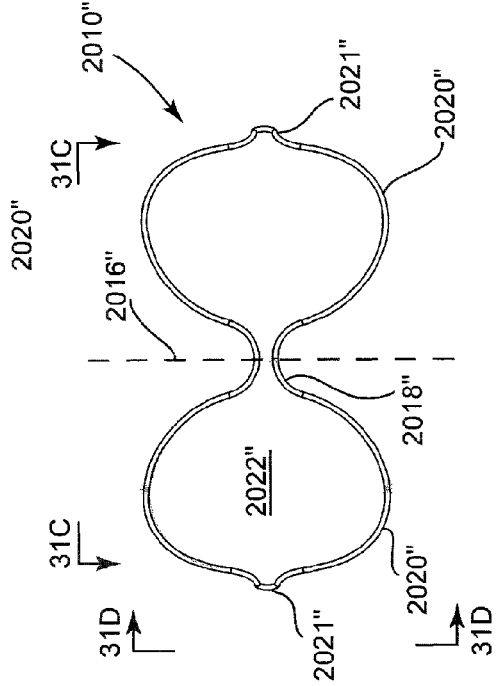

With particular reference to FIGS. 30C and 30D, using the suture 2030, one half of the appliance 2012 is then pulled through the opening OP through or behind the ligament (ALL) with the curve of the central region 2018 facing in the anterior direction. Initially, the first narrow tip 2021a is pulled through or behind the ligament, which may cause the narrow tip 2021a to compress vertically to pass through the opening created by the needle 2030 (the size of the opening OP shown not being to scale merely for clarity). As best shown in FIG. 30C, as the first broadened region 2020a is pulled through or behind the ligament (ALL), the design of the appliance 2012 allows the broadened region 2020a to compress vertically, e.g., into a collapsed configuration, to facilitate passage through the opening OP. As shown in FIG. 30D, once the broadened region 2020a passes completely through or behind the ligament (ALL), the broadened region 2020a may resiliently expand towards its relaxed state.

The appliance 2012 may be self locating, e.g., in that it is shaped and structured to gently unfold or spring into its appropriate position once it has been correctly placed. The suture 2032 is then cut and removed, leaving the appliance 2012 in position such that its central region 2018 remains within the opening OP through or behind the ligament (ALL). The portions of the loop element 2014 defining the central region 2018 may extend substantially parallel to one another in or behind the ligament (ALL), and the two broadened regions 2020 may rest against the surface of the mucosal layer of the posterior and lateral walls PW of the oropharyngeal region on both sides of the anterior longitudinal ligament. The most lateral ends of the appliance 2012 may also rest against the tongue.

Within a period of time, for example, within about one week, or two weeks or longer, after the surgical implantation, most or all of the appliance 2012 becomes submucosalized, such as shown in FIG. 30B, such that the appliance 2012 resides within the walls of the oropharyngeal region. No longer exposed on the interior surface of the pharyngeal walls, the appliance 2012 has essentially become an internal support structure which underlies the outer mucosal layer.

Optionally, if desired, the appliance 2012 may subsequently be removed from the patient, e.g., using a similar procedure used for implantation. For example, a tool (not shown) may be used to grab or otherwise be coupled to one of the narrow tips 2021, and the tip 2021 may be pulled to direct the opposite broadened region 2020 back through or behind the ligament (ALL). As the broadened region 2020 passes through or behind the ligament (ALL), the broadened region 2020 may again be compressed vertically, similar to that shown in FIG. 30C, until the broadened region 2020 is pulled completely through or behind the ligament (ALL), whereupon the entire appliance 2021 may be removed.

In an exemplary embodiment, an appliance 2012, such as that shown in FIGS. 29A-29E, may be selected for implantation in a patient. For example, the appliance 2012 may be made from 0.020" diameter round Nitinol wire and may have a length, i.e., from narrow tip 2021 to narrow tip 2021 along the horizontal plane, of about forty centimeters (40 mm).

The appliance may be inserted into the patient, while she is under general anesthesia, e.g., by a physician using direct visualization techniques, and a curved, U-shaped needle 2030 and suture 2032, as shown in FIG. 29G. A suture end opposite the needle 2030 may be tied to either extreme tip 2021 of the appliance 2012 using a knot (not shown) that may easily come apart when cut, for example, a fisherman's knot. The curved needle is introduced into the posterior wall of the patient's pharynx at about two centimeters (2.0 cm) to about two and a half centimeters (2.5 cm) above the epiglottis and approximately 0.2 cm lateral to the centerline. The needle is then carefully pushed through the anterior longitudinal ligament so that it emerges from the tissue at the same distance above the epiglottis and approximately 0.2 cm from the centerline of the side opposite that where it was introduced. The needle is pulled out of the tissue along with sufficient length of suture to allow it to be grasped and used to pull the appliance through the anterior longitudinal ligament, e.g., as described above with reference to FIGS. 30A-30D. Significant resistance on the needle 2030 and suture 2032 as they are pulled through the tissue may indicate that they have passed through the anterior longitudinal ligament. Using the suture 2032, one half of the appliance 2012 is then pulled through the anterior longitudinal ligament using the most lateral narrow tip 2021 to facilitate introduction and with the curved, central region 2018 facing in the anterior direction. While the appliance 2012 is being pulled through the tissue, the appliance 2012 may compress vertically, e.g., into a narrow, substantially linear delivery configuration that facilitates passage through the tissue. The appliance 2012 automatically unfolds or opens to regain its resting configuration once passed through the anterior longitudinal ligament. The suture 2032 is then cut and removed, leaving the appliance 2012 in position such that its central region 2018 rests in the anterior longitudinal ligament and the broadened regions 2020 rest against the surface of the mucosal layer of the posterior and lateral walls of the oropharyngeal region on both sides of the anterior longitudinal ligament. The appliance 2012 thus may make approximately a one hundred eighty degree (180°) rotation around the posterior oropharynx. Alternatively, in some instances, it may be more desirable for the appliance 2012 to be placed around or behind the anterior longitudinal ligament rather than being inserted through the ligament. The appliance 2012 may also extend beyond one hundred eighty degrees (180°), e.g., to provide resistance against posterior collapse of the tongue. After the appliance 2012 has been implanted and its position checked and verified to be acceptable, the procedure may be completed and the patient observed using conventional procedures.

After time, the appliance 2012 may become submucosalized, e.g., as shown in FIG. 30B. Upon subsequent direct examination of the patient, for example, it may be found that the broadened regions 2020 of the appliance 2012 on both sides of the anterior longitudinal ligament are not visible against the surfaces of the right and left oropharyngeal wall. Thus, the appliance 2012 may be located beneath the outer mucosal layer.

After the patient recovers from the surgery, she may no longer notice the presence of the appliance 2012 in her throat, even upon swallowing. Moreover, the patient may be able to achieve greater quality sleep at night due the implant, which may increase the patient's energy, e.g., during ordinary activities during the day.

In another embodiment, the apparatus may include an element that provides a magnetic opening force against collapsing pharyngeal, for example, oropharyngeal, tissues. For example, the apparatus may include an appliance, such as those described elsewhere herein, that is at least partially magnetized. More specifically, the apparatus may include two or more magnetic elements having like poles facing one another to create a magnetic field that may be utilized to provide a useful opening force to the pharyngeal, for example, oropharyngeal, region.

In yet another aspect, methods are provided for maintaining patency of a pharyngeal region, for example, the oropharyngeal region, in order to substantially reduce the occurrence of sleep apnea and/or snoring. These methods may include one or more of supporting, strengthening, reinforcing, and/or stiffening tissues of the region that are subject to collapse during natural sleep. For example, this may be accomplished by using one or more of the following: injecting an agent into the tissues, e.g., to cause partial necrosis of portions of the tissues in the region, thereby stiffening the region; injecting a liquid or gel agent into the tissues that solidifies within the tissues to provide a reinforcement against collapse of the region; mechanically or chemically irritating the tissues to cause a tissue reaction that firms the tissues of the region; and/or applying a wave energy to the tissues to cause a tissue reaction that firms the tissues of the region, for example, but not limited to ultrasonic energy, radiofrequency energy, thermal energy (either adding thermal energy to the tissues or chilling the tissue by removing thermal energy). Combinations of two or more of these steps may be advantageously employed.

An exemplary method for maintaining patency of a pharyngeal region generally includes providing an implant, for example elongated element 1401 shown in FIGS. 24 and 25, in a substantially flat or precurved configuration. The implant may include a body portion and end portions spaced apart by the body portion. The implant may be implanted, at least partially submucosally, within the pharyngeal region, e.g., within the oropharyngeal region, such that the implant is effective to provide a substantially constant force against at least a portion of each of the lateral walls of the region.

The step of implanting may include implanting the implant into the pharyngeal region such that the implant is substantially entirely submucosally implanted in the pharyngeal region. For example, the member may be implanted into oropharyngeal tissues, e.g., directly beneath the mucosal layer, by using a curved surgical needle to weave the member into and beneath the submucosal tissue.

In a related method, the method may include implanting an appliance, such as appliance 2012 shown in FIGS. 29A-29E, into the pharyngeal region of a patient, in a location generally adjacent the epiglottis. The appliance 2012 may be implanted through the lateral pharyngeal walls such that the appliance 2012 is located with broadened regions 2020 of the appliance 2012 overlying the lateral walls and generally narrow central region 2018 is located posterior to the pharynx, such as shown in FIG. 29E and FIG. 30A. The method further includes placing the appliance 2012 at the surface of the mucosa with pressure against the mucosa allowing the appliance 2012 to submucosalize into the pharyngeal walls over a period of days or weeks as seen in FIG. 30B.

In another embodiment, a method is provided that includes providing an apparatus in the oropharyngeal region of the human or animal, for purposes other than surgery. The apparatus may be effective in treating sleep apnea and/or snoring and/or in maintaining patency of the oropharyngeal region during natural sleep of the human or animal, without causing substantial interference with one or more natural functions of the epiglottis.

Each of the apparatus for treating sleep apnea and/or snoring described and shown elsewhere herein are suitable for use in any of the methods described herein. It is to be appreciated, however, that the apparatus used for performing the methods described herein may take other forms as well. For example, it is contemplated herein that a conventional stent may be used in maintaining the airway in the pharyngeal region, for example, the oropharyngeal region in an open state, and such use is considered to be within the scope of the methods described herein. The apparatus used in the methods described herein may be devices, for example but not limited to, a conventional stent, sized and structured for placement in another region of the human or animal other than the pharyngeal region, for example, the oropharyngeal region.

In another embodiment, a method for maintaining patency of a pharyngeal region of a patient includes providing an apparatus in a first configuration, for example a rolled, coiled, or otherwise compressed configuration; inserting the apparatus into the oropharyngeal region, for example through the oral or nasal cavity of the patient while the apparatus is in the compressed configuration; and, thereafter, allowing the apparatus to reconfigure or expand towards its original relaxed configuration, for example, defining a substantially cuff shape, C-shape, or other suitable deployed configuration, within the oropharyngeal region.

Any suitable deployment assembly useful for inserting the apparatus through the mouth or oral cavity, or nasal cavity of a patient and into the oropharyngeal region may be utilized in accordance with the methods described herein.

For example, a suitable deployment assembly includes an outer tube (e.g., about ten millimeters (10 mm) diameter) and inner tube (e.g., about eight millimeters (8 mm) diameter) disposed within the outer tube (not shown). A retaining clip may be used to fix the tubes in place with respect to each other. The appliance, for example in a rolled configuration or an axially compressed and/or substantially straightened configuration, may be provided within the outer tube at a distal portion thereof Graspers, having a manually manipulable proximal portion may be provided through the tubes for assisting in positioning or removal of the appliance.

During insertion through the mouth or oral cavity of the patient, the deployment assembly may be advanced past the tongue of the patient until the inner diameter of the outer tube and the rolled appliance passes into the oropharyngeal region. The retaining clip may then be removed from the inner tube. The graspers may be used to facilitate repositioning of the appliance as necessary or desirable. The appliance may be deployed by retraction of the outer tube relative to the inner tube. Optionally, if desired or necessary, the graspers may be used subsequently to remove the appliance if desired.

In a more specific embodiment, the following method is provided. This method generally includes providing a flat or pre-curved member (for example, appliance 110, 210, 310, 410, 510, 610, 710, 810, 910, 1010, 1110 or 1120 shown in the drawings), pulling end portions of the flat or pre-curved member together to form a folded member and holding or temporarily securing the end portions together by means of a grasper, clamp, hemostat, suture (for example, a bioresorbable suture), and/or suitable means for temporarily holding the end portions together in contact with one another. The method further includes placing the member in the folded or pinched configuration, into the oropharyngeal region, for example by way of the oral or nasal cavity of the patient, and releasing the end portions, thereby allowing the member to expand radially within the oropharyngeal region to provide a substantially constant radial force against the lateral walls of the oropharyngeal region and/or the base of the tongue.

The method may further include the step of repositioning the member while the member is located within the oropharyngeal region and/or the step of removing the member therefrom. This may be accomplished by folding the member into a rolled or pinched configuration and withdrawing the member from the body region.

In another embodiment, a patient may be treated, e.g., who experiences snoring with apneic pauses, severe daytime hypersomnolence with narcolepsy, and the like. If desired, a polysomnography may be performed, e.g., to indicate a Respiratory Disturbance Index (RDI) for the patient, which may show severe desaturation, bradycardia, and/or partial or complete absence of stage 3, stage 4, and REM sleep.

An implant, such as appliance 1400 shown in FIG. 25 may be selected, e.g., having a length of about seventy millimeters (70 mm), a width of about 1.0 mm, and a thickness of about 0.0075 inches (about 0.2 mm), for submucosal implantation.

Under general or local anesthesia, e.g., using direct laryngoscopy techniques, the appliance 1400 may be introduced into the submucosal tissues beginning in the right lateral pharyngeal region, particularly the right lateral oropharyngeal region. The appliance may be introduced submucosally using a curved surgical needle that may be used to pull the appliance into the tissues in a manner that causes the appliance to be substantially concealed within the tissues, with little or no exposure of any portion of the appliance postsurgically.

The appliance may be guided medially and inferiorly, traveling around the posterior oropharyngeal region and ultimately into the submucosal tissues of the tongue base. The tongue base is then traversed and the appliance is brought back along the right lateral oropharyngeal wall. The appliance thus makes at least one complete rotation around the pharynx.

In another embodiment, an implant, such as appliance 1400 shown in FIG. 25, may be selected for implantation in a patient. In this example, the appliance 1400 is made from Nitinol and has a length of about forty millimeters (40 mm), a width of 1.25 mm and a thickness of about 0.5 mm.

Under general or local anesthesia, e.g., using direct laryngoscopy techniques, the appliance may be introduced into the submucosal tissues beginning in the right lateral oropharyngeal region. The appliance is then guided medially and inferiorly, traveling around the posterior oropharyngeal region and ultimately into the submucosal tissues of the left lateral oropharynx. The appliance does not traverse the tongue. The appliance thus makes about a one hundred eighty degree (180°) rotation around the oropharynx.

While this invention has been described with respect to various specific examples and embodiments, it is to be understood that the invention is not limited thereto and that it can be variously practiced within the scope of the following claims.

We claim:

1. An apparatus for implantation within an oropharyngeal region adjacent a ligament, comprising:
    an implant comprising a substantially continuous loop structure comprising a central region between first and second regions in a horizontal plane;
    the first and second regions being foldable towards one another within the horizontal plane such that the implant defines a generally "C" shape about a vertical axis extending from the horizontal plane, the first and second regions being biased to unfold away from the vertical axis within the horizontal plane such that the first and second regions apply a force to dilate tissue adjacent the oropharyngeal region when the implant is disposed within the oropharyngeal region;
    the central region of the implant being vertically narrow relative to the first and second regions, at least one of the first and second regions being compressible vertically to allow the at least one of the first and second regions to be directed through or behind the ligament adjacent the oropharyngeal region such that the central region is disposed within or behind the ligament, the at least one of the first and second regions being resiliently expandable after passing through or behind the ligament; and
    a filament coupled to the at least one of the first and second regions, a free end of the filament being advanceable through or behind the ligament for guiding the at least one of the first and second regions through or behind the ligament.

2. The apparatus of claim 1, wherein the central region and the first and second regions are biased to curve around the vertical axis within the horizontal plane.

3. The apparatus of claim 2, wherein the central region and the first and second regions are biased to a radius of curvature greater than sixteen millimeters.

4. The apparatus of claim 1, wherein at least one of the first and second regions terminates in a vertically narrow tip to facilitate introduction of the at least one of the first and second regions through or behind the ligament.

5. The apparatus of claim 1, further comprising a needle coupled to the free end of the filament, the needle having a sharpened tip for penetrating through or behind the ligament for advancing the filament through or behind the ligament.

6. The apparatus of claim 1, wherein the central region of the implant is biased to curve around the vertical axis, and wherein the first and second regions are biased to curve away from the vertical axis within the horizontal plane.

7. A system for treating sleep apnea, snoring, or other breathing disorders within an oropharyngeal region adjacent a ligament, comprising:
    an implant including a central region between first and second end regions within a horizontal plane; and
    a needle coupled to the first end region by a filament for insertion through a ligament adjacent an oropharyngeal region;
    the central region being vertically narrow and flanked by the first and second end regions, which are vertically wide compared to the central region to define a generally bow-tie shape in a relaxed state, at least the first end region being compressible vertically to allow the first region to be directed through or behind the ligament adjacent the oropharyngeal region when the needle and filament are inserted through or behind the ligament such that the central region is disposed within or behind the ligament, the first region being resiliently expandable after passing through or behind the ligament.

8. The system of claim 7, wherein the first and second regions are foldable towards one another within the horizontal plane such that the implant defines a generally "C" shape about a vertical axis extending from the horizontal plane, the first and second regions being biased to unfold away from the vertical axis within the horizontal plane such that the first and second regions apply a force to dilate tissue adjacent the oropharyngeal region when the implant is disposed within the oropharyngeal region.

9. An apparatus for treating at least one of sleep apnea and snoring in a human or an animal having an oropharyngeal region, the apparatus comprising:
an appliance sized and structured to be placed in the oropharyngeal region and being effective in treating at least one of sleep apnea and snoring, the appliance comprising substantially opposing elongated elements spaced apart from one another and coupled together at opposing end regions, thereby forming an open loop configuration enclosing an open area between the elongated elements and defining a relatively narrow central region located midway between the end regions and relatively wide regions between the centrally located region and the end regions, each of the elongated elements having a generally centrally located portion flanked by broadened portions extending from the centrally located portion to respective opposing end regions, the centrally located portion of one elongated element located substantially more closely to the centrally located portion of the other elongated element to define the centrally located region and the broadened portions of one elongated element spaced further from the broadened portions of the other elongated element to define the relatively wide regions between the centrally located region and the end regions, thereby defining a bow-tie shape.

10. The apparatus of claim 9, wherein the two elongated elements comprise a resilient wire.

11. The apparatus of claim 9, wherein the appliance is compressible to a constrained configuration when being introduced into an oropharyngeal region, and is biased to a relaxed configuration when the appliance is so placed in an oropharyngeal region that is larger than the constrained configuration.

12. The apparatus of claim 9, wherein the appliance has a length between about thirty millimeters (30 mm) and about one hundred millimeters (100 mm).

13. The apparatus of claim 12, wherein the appliance has a height between about forty millimeters (40 mm) and about ninety millimeters (90 mm).

14. A method for treating sleep apnea or snoring within an oropharyngeal region adjacent an anterior longitudinal ligament located between the oropharyngeal region and the spinal column, the method comprising:
introducing an implant into the oropharyngeal region, the implant comprising a central region between first and second regions, the central region being vertically narrow relative to the first and second regions; and
introducing the first region through an opening through or behind the ligament, the first region compressed vertically from a relaxed configuration as the first region passes through the opening, until the first region passes through the opening, whereupon the first region resiliently expands towards the relaxed configuration, the central region remaining within the opening to maintain the implant within the oropharyngeal region, the first and second regions applying a force to tissue adjacent the oropharyngeal region.

15. The method of claim 14, wherein the implant comprises an endless loop defining the central region and the first and second regions that are relatively wider than the central region.

16. The method of claim 14, further comprising inserting a needle through or behind the ligament to create the opening, the needle being coupled to the first region by a filament such that the first region is introduced through the opening by pulling the filament after the needle is inserted through or behind the ligament.

17. The method of claim 14, wherein introducing the first region through the opening comprises passing the first region into a lateral or posterior wall of the oropharyngeal region and through or adjacent the ligament.

18. The method of claim 14, wherein the first and second regions are located against or within the posterior and right and left lateral walls of the oropharyngeal region when the central region is disposed within the opening to dilate the tissue adjacent the oropharyngeal region.

19. A method for controlling sleep apnea or snoring in a human or animal having an oropharyngeal region and an anterior longitudinal ligament located between the oropharyngeal region and the spinal column, the method comprising:
providing a flexible, resilient appliance sized and structured to be positioned in an oropharyngeal region of a patient, the appliance comprising substantially opposing elongated elements together forming a loop having a generally narrow central region and first and second end regions that are relatively wider than the central region;
introducing the appliance into the oropharyngeal region by passing the appliance into a lateral or posterior wall of the oropharyngeal region and through or adjacent the anterior longitudinal ligament of the patient such that, upon the appliance being so positioned in the oropharyngeal region, the generally narrow central region is at least partially beneath the posterior wall of the oropharyngeal region and the first and second end portions are located against or within the posterior and right and left lateral walls of the oropharyngeal region.

20. The method of claim 19, wherein the appliance has a resiliency that allows the appliance to be collapsed into a substantially linear configuration during introduction into the oropharyngeal region.

21. The method of claim 19, wherein the appliance is substantially self-positioning once the appliance has been introduced into the oropharyngeal region.

22. The method of claim 19, wherein the appliance has flexibility and resiliency that allow the appliance to be introduced into an oropharyngeal region through an incision of less than about five millimeters (5 mm).

23. The method of claim 19, wherein introducing the appliance comprises using a curved surgical needle.

* * * * *